(12) United States Patent
Saliman et al.

(10) Patent No.: US 9,913,638 B2
(45) Date of Patent: *Mar. 13, 2018

(54) TRANSOSTEAL ANCHORING METHODS FOR TISSUE REPAIR

(71) Applicant: Ceterix Orthopaedics, Inc., Fremont, CA (US)

(72) Inventors: Justin D. Saliman, Los Angeles, CA (US); John G. McCutcheon, Menlo Park, CA (US); Michael J. Hendricksen, Redwood City, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/451,293

(22) Filed: Aug. 4, 2014

(65) Prior Publication Data

US 2015/0039030 A1 Feb. 5, 2015
US 2017/0181738 A9 Jun. 29, 2017

Related U.S. Application Data

(63) Continuation-in-part of application No. 13/893,209, filed on May 13, 2013, now Pat. No. 8,888,848,
(Continued)

(51) Int. Cl.
*A61B 17/04* (2006.01)
*A61F 2/08* (2006.01)
(Continued)

(52) U.S. Cl.
CPC ...... *A61B 17/0401* (2013.01); *A61B 17/0642* (2013.01); *A61B 17/06166* (2013.01); *A61F 2/0811* (2013.01); *A61F 2002/0882* (2013.01)

(58) Field of Classification Search
CPC ............ A61F 2/0811; A61F 2002/0858; A61F 2002/0882; A61F 2002/0841;
(Continued)

(56) References Cited

U.S. PATENT DOCUMENTS 1,037,864 A 9/1912 Carlson et al.
2,738,790 A 3/1956 Todt, Sr. et al.
(Continued)

FOREIGN PATENT DOCUMENTS

CN 201263696 Y 7/2009
CN 101961256 A 2/2011
(Continued)

OTHER PUBLICATIONS

Dictionary definition of "adjacent". <http://www.dictionary.com/browse/adjacent> Accessed Apr. 5, 2016.*
(Continued)

*Primary Examiner* — Katherine M Shi
(74) *Attorney, Agent, or Firm* — Shay Glenn LLP

(57) ABSTRACT

Described herein are methods and apparatuses for use in repair of a patient's tissue by connecting the tissue to the bone using a transosteal tunnel and anchor configured to pass through the transosteal tunnel. In particular, described herein are methods of repairing an anterior cruciate ligament (ACL) and torn meniscal root. These anchoring apparatuses and method of using them are particularly well suited for use with the low-profile suture passers described herein, since these suture passers may allow access to previously inaccessible regions of the knee (or other body regions).

14 Claims, 38 Drawing Sheets

Related U.S. Application Data which is a continuation of application No. 13/347,184, filed on Jan. 10, 2012, now Pat. No. 8,500,809.

(60) Provisional application No. 61/862,414, filed on Aug. 5, 2013, provisional application No. 61/431,293, filed on Jan. 10, 2011.

(51) Int. Cl.
  *A61B 17/064* (2006.01)
  *A61B 17/06* (2006.01)

(58) Field of Classification Search
  CPC ...... A61F 2002/0852; A61F 2002/0864; A61F 2002/087; A61F 2/0805; A61B 17/0401; A61B 2017/0414; A61B 2017/044; A61B 2017/0445; A61B 17/0469
  USPC ............ 606/13.12, 13.14; 623/144–148, 232
  See application file for complete search history.

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A * | 5/1997 | Beck, Jr. ............... A61F 2/0811 606/232 |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |

(56) References Cited

U.S. PATENT DOCUMENTS

| | | | |
|---|---|---|---|
| 6,099,568 A * | 8/2000 | Simonian | A61B 17/0401 623/13.11 |
| 6,113,610 A | 9/2000 | Poncet | |
| 6,126,666 A | 10/2000 | Trapp et al. | |
| 6,129,741 A | 10/2000 | Wurster et al. | |
| 6,139,556 A | 10/2000 | Kontos | |
| 6,152,934 A | 11/2000 | Harper et al. | |
| 6,159,224 A | 12/2000 | Yoon | |
| 6,190,396 B1 | 2/2001 | Whitin et al. | |
| 6,221,085 B1 | 4/2001 | Djurovic | |
| 6,231,606 B1 * | 5/2001 | Graf | A61F 2/0811 606/232 |
| 6,238,414 B1 | 5/2001 | Griffiths | |
| 6,264,694 B1 | 7/2001 | Weiler | |
| 6,277,132 B1 | 8/2001 | Brhel | |
| 6,322,570 B1 | 11/2001 | Matsutani et al. | |
| 6,325,808 B1 | 12/2001 | Bernard et al. | |
| 6,355,050 B1 | 3/2002 | Andreas et al. | |
| 6,368,334 B1 | 4/2002 | Sauer | |
| 6,368,343 B1 | 4/2002 | Bonutti et al. | |
| 6,443,963 B1 | 9/2002 | Baldwin et al. | |
| 6,511,487 B1 | 1/2003 | Oren et al. | |
| 6,533,795 B1 | 3/2003 | Tran et al. | |
| 6,533,796 B1 | 3/2003 | Sauer et al. | |
| 6,551,330 B1 | 4/2003 | Bain et al. | |
| 6,585,744 B1 | 7/2003 | Griffith | |
| 6,626,917 B1 | 9/2003 | Craig | |
| 6,626,929 B1 | 9/2003 | Bannerman | |
| 6,638,283 B2 | 10/2003 | Thal | |
| 6,638,286 B1 | 10/2003 | Burbank et al. | |
| 6,641,592 B1 | 11/2003 | Sauer et al. | |
| 6,719,765 B2 | 4/2004 | Bonutti | |
| 6,723,107 B1 | 4/2004 | Skiba et al. | |
| 6,770,084 B1 | 8/2004 | Bain et al. | |
| 6,833,005 B1 * | 12/2004 | Mantas | A61B 17/1675 606/232 |
| 6,896,686 B2 | 5/2005 | Weber | |
| 6,921,408 B2 | 7/2005 | Sauer | |
| 6,923,806 B2 | 8/2005 | Hooven et al. | |
| 6,923,819 B2 | 8/2005 | Meade et al. | |
| 6,936,054 B2 | 8/2005 | Chu | |
| 6,972,027 B2 | 12/2005 | Fallin et al. | |
| 6,984,237 B2 | 1/2006 | Hatch et al. | |
| 6,991,635 B2 | 1/2006 | Takamoto et al. | |
| 6,997,931 B2 | 2/2006 | Sauer et al. | |
| 6,997,932 B2 | 2/2006 | Dreyfuss et al. | |
| 7,004,951 B2 | 2/2006 | Gibbens, III | |
| 7,029,480 B2 | 4/2006 | Klein et al. | |
| 7,029,481 B1 | 4/2006 | Burdulis, Jr. et al. | |
| 7,041,111 B2 | 5/2006 | Chu | |
| 7,063,710 B2 | 6/2006 | Takamoto et al. | |
| 7,087,060 B2 | 8/2006 | Clark | |
| 7,112,208 B2 | 9/2006 | Morris et al. | |
| 7,118,583 B2 | 10/2006 | O'Quinn et al. | |
| 7,131,978 B2 | 11/2006 | Sancoff et al. | |
| 7,153,312 B1 | 12/2006 | Torrie et al. | |
| 7,166,116 B2 | 1/2007 | Lizardi et al. | |
| 7,175,636 B2 | 2/2007 | Yamamoto et al. | |
| 7,211,093 B2 | 5/2007 | Sauer et al. | |
| 7,232,448 B2 | 6/2007 | Battles et al. | |
| 7,235,086 B2 | 6/2007 | Sauer et al. | |
| 7,311,715 B2 | 12/2007 | Sauer et al. | |
| 7,344,545 B2 | 3/2008 | Takemoto et al. | |
| 7,390,328 B2 | 6/2008 | Modesitt | |
| 7,481,817 B2 | 1/2009 | Sauer | |
| 7,481,826 B2 | 1/2009 | Cichocki | |
| 7,491,212 B2 | 2/2009 | Sikora et al. | |
| 7,588,583 B2 | 9/2009 | Hamilton et al. | |
| 7,594,922 B1 | 9/2009 | Goble et al. | |
| 7,632,284 B2 | 12/2009 | Martinek et al. | |
| 7,674,276 B2 | 3/2010 | Stone et al. | |
| 7,717,927 B2 | 5/2010 | Hahn et al. | |
| 7,722,630 B1 | 5/2010 | Stone et al. | |
| 7,731,727 B2 | 6/2010 | Sauer | |
| 7,736,372 B2 | 6/2010 | Reydel et al. | |
| 7,749,236 B2 | 7/2010 | Oberlaender et al. | |
| 7,842,050 B2 | 11/2010 | Diduch et al. | |
| 7,879,046 B2 | 2/2011 | Weinert et al. | |
| 7,883,519 B2 | 2/2011 | Oren et al. | |
| 7,951,147 B2 | 5/2011 | Privitera et al. | |
| 7,951,159 B2 | 5/2011 | Stokes et al. | |
| 7,972,344 B2 | 7/2011 | Murray et al. | |
| 8,298,230 B2 | 10/2012 | Sutter et al. | |
| 8,394,112 B2 | 3/2013 | Nason | |
| 8,398,673 B2 | 3/2013 | Hinchliffe et al. | |
| 8,449,533 B2 | 5/2013 | Saliman et al. | |
| 8,465,505 B2 | 6/2013 | Murillo et al. | |
| 8,500,809 B2 | 8/2013 | Saliman | |
| 8,562,631 B2 | 10/2013 | Saliman | |
| 8,632,563 B2 | 1/2014 | Nagase et al. | |
| 8,647,354 B2 | 2/2014 | Domingo | |
| 8,663,253 B2 | 3/2014 | Saliman | |
| 8,702,731 B2 | 4/2014 | Saliman | |
| 8,808,299 B2 | 8/2014 | Saliman et al. | |
| 8,821,518 B2 | 9/2014 | Saliman | |
| 2001/0041938 A1 * | 11/2001 | Hein | A61F 2/0811 623/13.13 |
| 2002/0169477 A1 | 11/2002 | Demopulos et al. | |
| 2003/0023250 A1 | 1/2003 | Watschke et al. | |
| 2003/0065336 A1 | 4/2003 | Xiao | |
| 2003/0065337 A1 | 4/2003 | Topper et al. | |
| 2003/0078599 A1 | 4/2003 | O'Quinn et al. | |
| 2003/0078617 A1 | 4/2003 | Schwartz et al. | |
| 2003/0181926 A1 | 9/2003 | Dana et al. | |
| 2003/0204194 A1 | 10/2003 | Bittar | |
| 2003/0216755 A1 | 11/2003 | Shikhman et al. | |
| 2003/0233106 A1 | 12/2003 | Dreyfuss | |
| 2004/0117014 A1 * | 6/2004 | Bryant | A61F 2/08 623/13.12 |
| 2004/0249392 A1 | 12/2004 | Mikkaichi et al. | |
| 2004/0249394 A1 | 12/2004 | Morris et al. | |
| 2004/0267304 A1 | 12/2004 | Zannis et al. | |
| 2005/0033319 A1 | 2/2005 | Gambale et al. | |
| 2005/0033365 A1 | 2/2005 | Courage | |
| 2005/0043746 A1 | 2/2005 | Pollak et al. | |
| 2005/0080434 A1 | 4/2005 | Chung et al. | |
| 2005/0090837 A1 | 4/2005 | Sixto, Jr. et al. | |
| 2005/0090840 A1 | 4/2005 | Gerbino et al. | |
| 2005/0154403 A1 | 7/2005 | Sauer et al. | |
| 2005/0228406 A1 | 10/2005 | Bose | |
| 2005/0288690 A1 | 12/2005 | Bourque et al. | |
| 2006/0020272 A1 | 1/2006 | Gildenberg | |
| 2006/0047289 A1 | 3/2006 | Fogel | |
| 2006/0084974 A1 | 4/2006 | Privitera et al. | |
| 2006/0282098 A1 | 12/2006 | Shelton et al. | |
| 2007/0032799 A1 | 2/2007 | Pantages et al. | |
| 2007/0038230 A1 | 2/2007 | Stone et al. | |
| 2007/0156174 A1 | 7/2007 | Kaiser et al. | |
| 2007/0185532 A1 | 8/2007 | Stone et al. | |
| 2007/0219571 A1 | 9/2007 | Balbierz et al. | |
| 2007/0250118 A1 | 10/2007 | Masini | |
| 2007/0260260 A1 | 11/2007 | Hahn et al. | |
| 2007/0260278 A1 | 11/2007 | Wheeler et al. | |
| 2008/0086147 A1 | 4/2008 | Knapp | |
| 2008/0091219 A1 | 4/2008 | Marshall et al. | |
| 2008/0097482 A1 | 4/2008 | Bain et al. | |
| 2008/0097489 A1 | 4/2008 | Goldfarb et al. | |
| 2008/0140091 A1 | 6/2008 | DeDeyne et al. | |
| 2008/0140094 A1 | 6/2008 | Schwartz et al. | |
| 2008/0228204 A1 | 9/2008 | Hamilton et al. | |
| 2008/0234725 A1 | 9/2008 | Griffiths et al. | |
| 2008/0243147 A1 | 10/2008 | Hamilton et al. | |
| 2008/0269783 A1 | 10/2008 | Griffith | |
| 2008/0275553 A1 * | 11/2008 | Wolf | A61B 17/0401 623/13.14 |
| 2008/0294256 A1 | 11/2008 | Hagan et al. | |
| 2009/0012520 A1 | 1/2009 | Hixson et al. | |
| 2009/0012538 A1 | 1/2009 | Saliman | |
| 2009/0018554 A1 | 1/2009 | Thorne et al. | |
| 2009/0062816 A1 | 3/2009 | Weber | |
| 2009/0062819 A1 | 3/2009 | Burkhart et al. | |
| 2009/0105729 A1 | 4/2009 | Zentgraf | |
| 2009/0105751 A1 | 4/2009 | Zentgraf | |
| 2009/0112232 A1 | 4/2009 | Crainich et al. | |

(56) References Cited

U.S. PATENT DOCUMENTS

| | | |
|---|---|---|
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1* | 11/2011 | Denham ............ A61B 17/0401 606/228 |
| 2012/0101524 A1* | 4/2012 | Bennett .............. A61B 17/0401 606/232 |
| 2012/0179254 A1* | 7/2012 | Saliman ............. A61B 17/0401 623/13.12 |
| 2012/0239062 A1 | 9/2012 | Saliman et al. |
| 2012/0283750 A1 | 11/2012 | Saliman et al. |
| 2012/0283753 A1 | 11/2012 | Saliman et al. |
| 2012/0303046 A1 | 11/2012 | Stone et al. |
| 2013/0072948 A1 | 3/2013 | States, III et al. |
| 2013/0085512 A1* | 4/2013 | Wyman .............. A61B 17/0401 606/139 |
| 2013/0253647 A1 | 9/2013 | Saliman et al. |
| 2013/0331865 A1 | 12/2013 | Murillo et al. |
| 2014/0074157 A1 | 3/2014 | Hirotsuka et al. |
| 2014/0188136 A1 | 7/2014 | Cournoyer et al. |
| 2014/0222029 A1 | 8/2014 | McCutcheon et al. |
| 2014/0222034 A1 | 8/2014 | Saliman |
| 2014/0236192 A1 | 8/2014 | Hendricksen et al. |
| 2014/0276981 A1 | 9/2014 | Hendricksen et al. |
| 2014/0276987 A1 | 9/2014 | Saliman |
| 2015/0034694 A1 | 2/2015 | Cappola |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2016/0192926 A1 | 7/2016 | Hendricksen et al. |
| 2016/0220244 A1 | 8/2016 | Murillo et al. |
| 2016/0242765 A1 | 8/2016 | George et al. |
| 2017/0027558 A1 | 2/2017 | Murillo et al. |
| 2017/0119372 A1 | 5/2017 | Peter et al. |

FOREIGN PATENT DOCUMENTS

| | | |
|---|---|---|
| EP | 0647431 A2 | 4/1995 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 7288848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |
| WO | WO 2015/095133 A1 | 6/2015 |

OTHER PUBLICATIONS

Hendricksen et al.; U.S. Appl. No. 14/681,528 entitled "Suture passers adapted for use in constrained regions," filed Apr. 8, 2015.

Hendricksen et al.; U.S. Appl. No. 14/697,494 entitled "Suture passers adapted for use in constrained regions," filed Apr. 27, 2015.

Murillo et al.; U.S. Appl. No. 14/572,485 entitled "Automatically reloading suture passer devices and methods," filed Dec. 16, 2014.

Saliman et al.; U.S. Appl. No. 14/546,942 entitled "Suture passer and method for hip labrum repair," filed Nov. 18, 2014.

George et al.; U.S. Appl. No. 14/608,057 entitled "Arthroscopic knot pusher and suture cutter," filed Jan. 28, 2015.

Hendricksen et al.; U.S. Appl. No. 14/659,471 entitled "Suture passer with radiused upper jaw," filed Mar. 16, 2015.

George et al.; U.S. Appl. No. 14/494,561 entitled "Arthroscopic knot pusher and suture cutter," filed Sep. 23, 2014.

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

Duerig, T. et al., "An overview of nitinol medical applications" Materials Science and Engineering A273-275, May 1999.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

(56) References Cited

OTHER PUBLICATIONS

Ma et al; "Biomechanical Evaluation of Arthroscopic Rotator Cuff Stitches," J Bone Joint Surg Am, Jun. 2004; vol. 86(6):1211-1216.
Medsfera; Suturing devices; accessed Dec. 4, 2012 at <http://www.medsfera.ru/shiv.html> 13 pages.
Nho et al; "Biomechanical fixation in Arthroscopic Rotator Cuff Repair," Arthroscopy: J of Arthroscop and Related Surg; vol. 23. No. 1, Jan. 2007: pp. 94-102.
Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Schneeberger, et al; "Mechanical Strength of Arthroscopic Rotator Cuff Repair Techniques: An in Vitro Study," J Bone Joint Surg Am., Dec. 2002; 84:2152-2160.
Smith&Nephew; Fast-Fix Meniscal Repair System (product webpage); 4 pgs.; downloaded Nov. 21, 2011 (http://endo.smith-nephew.com/fr/node.asp?NodeId=3562).
Strobel; Manual of Arthroscopic Surgery (1st Edition); Springer Verlag, Hiedelberg © 2002; pp. 127-129; Dec. 15, 2001.
USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.
USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.
Hirotsuka et al.; U.S. Appl. No. 15/132,211 entitled "Pre-tied surgical knots for use with suture passers," filed Apr. 18, 2016.
Murillo et al.; U.S. Appl. No. 15/216,482 entitled "Automatically reloading suture passer devices that prevent entanglement," filed Jul. 21, 2016.

\* cited by examiner

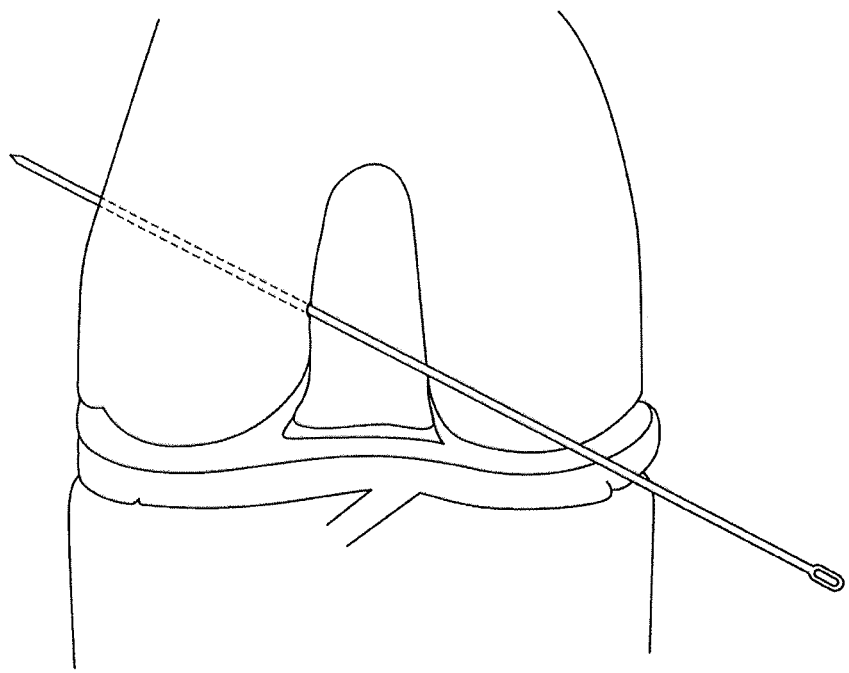
FIG. 3B
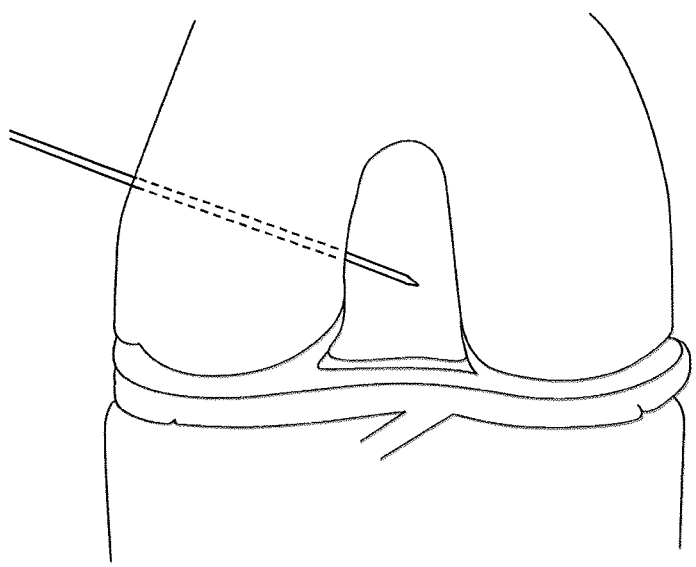
FIG. 3B1

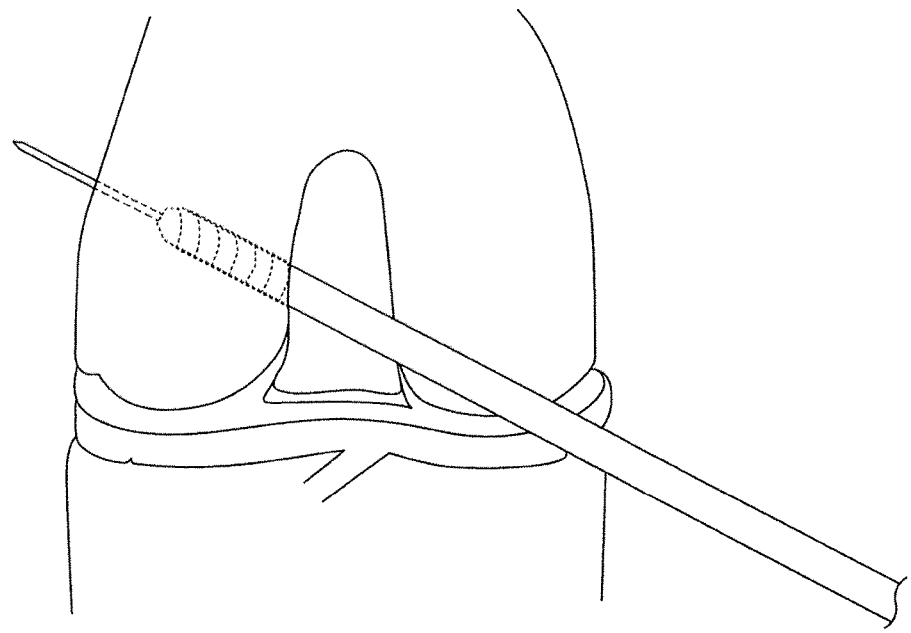
FIG. 3C
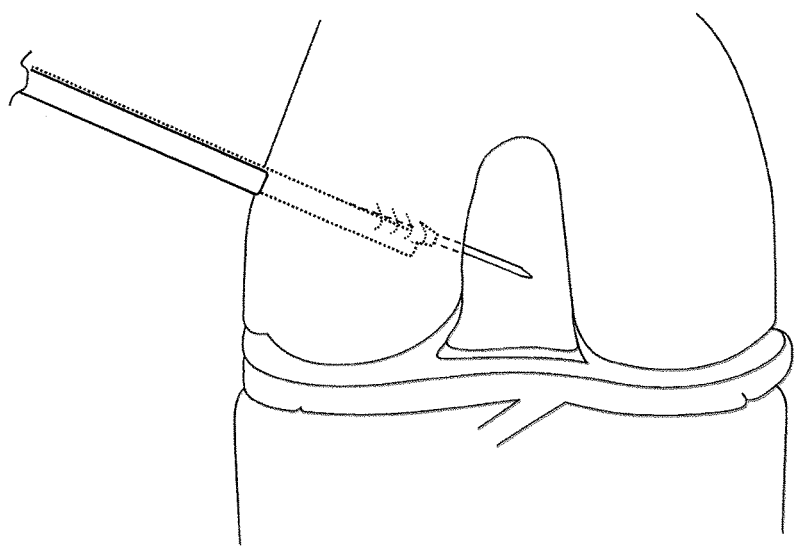
FIG. 3C1

Axial view of tunnel

FIG. 3F1

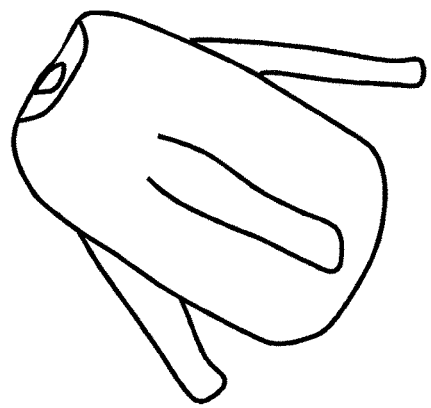
FIG. 6
FIG. 7A    FIG. 7B
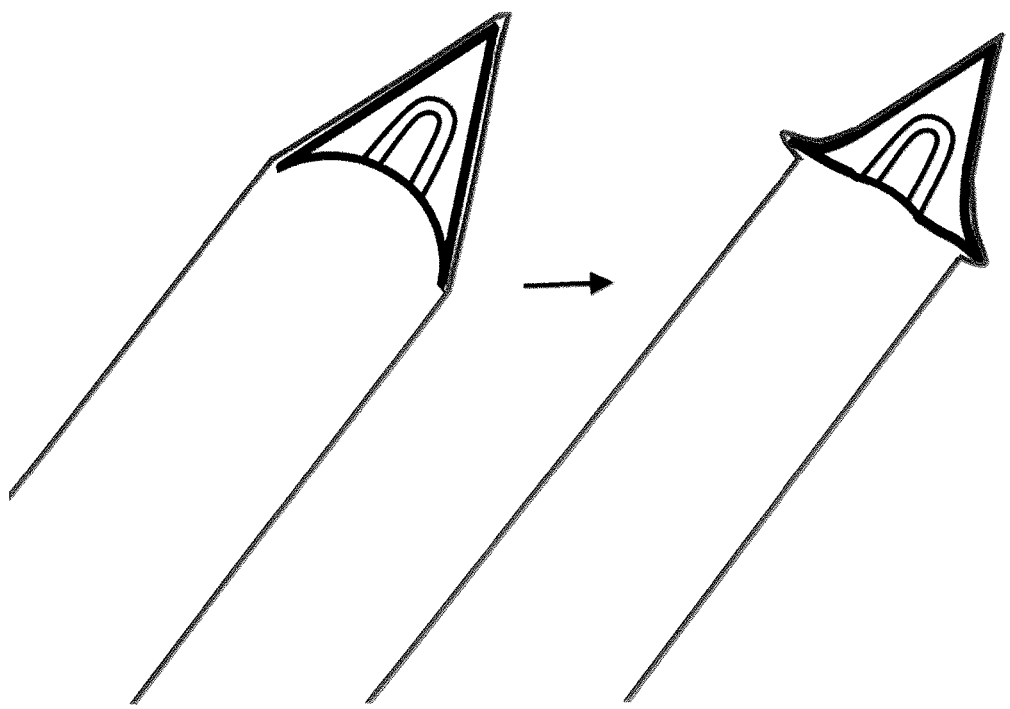

FIG. 10E1

Cinch suture in place to pull in and secure ligament (optional) fill tunnel to further secure anchor Trim all or some of the suture after it is locked into anchor Alternate anchor Alternate channel Peripheral pass Loop pass Central pass

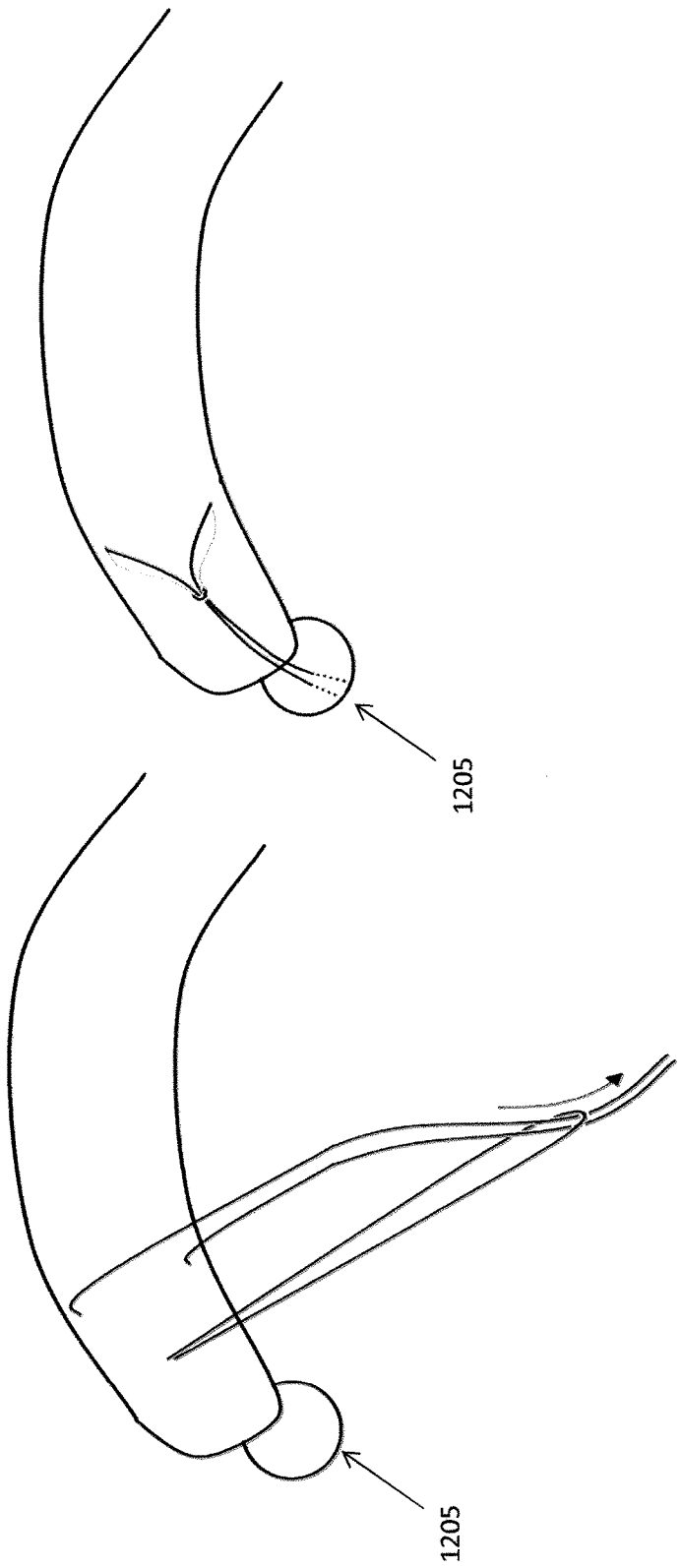
FIG. 13E Suture limbs pulled down into trough
FIG. 13D Suture limbs fed through loop

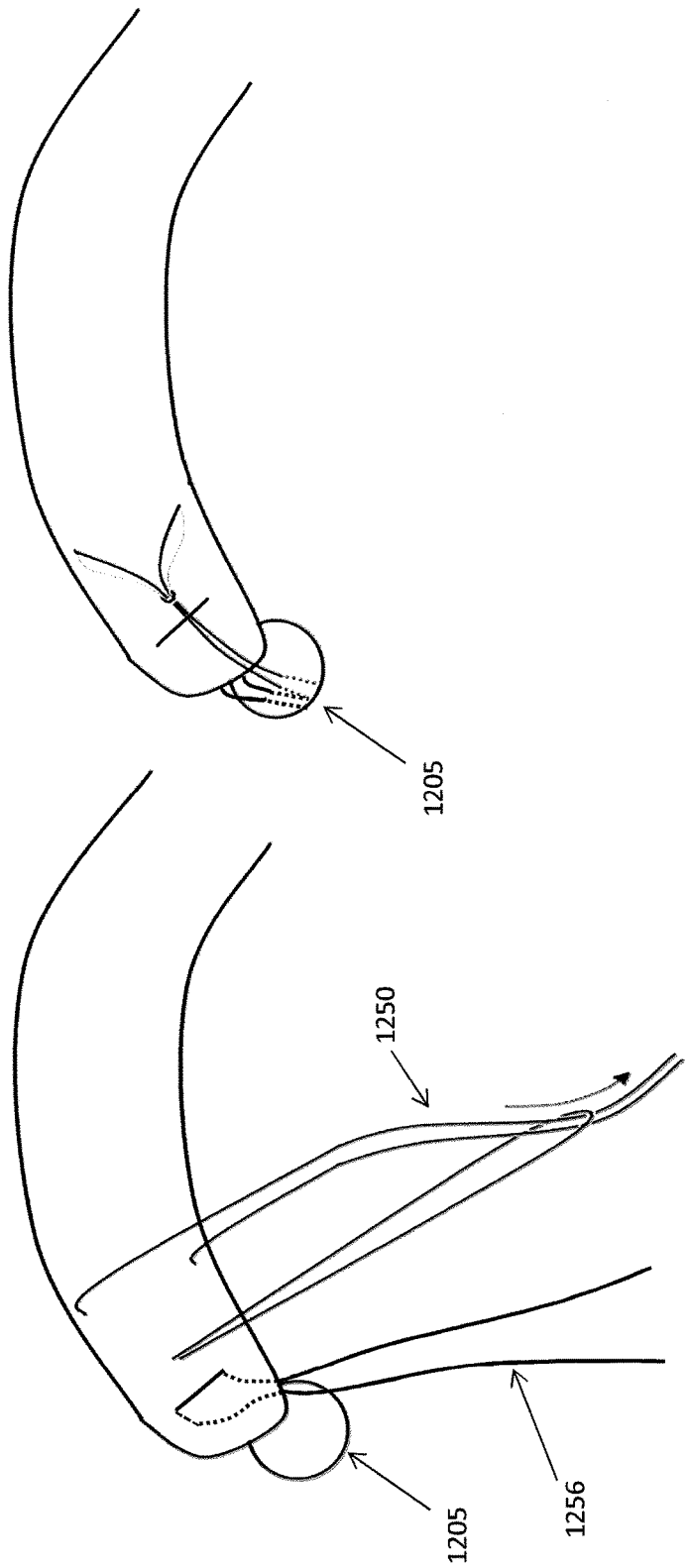
FIG. 13F  Simple stitch 1 and locking loop
FIG. 13G  All suture limbs pulled down into trough

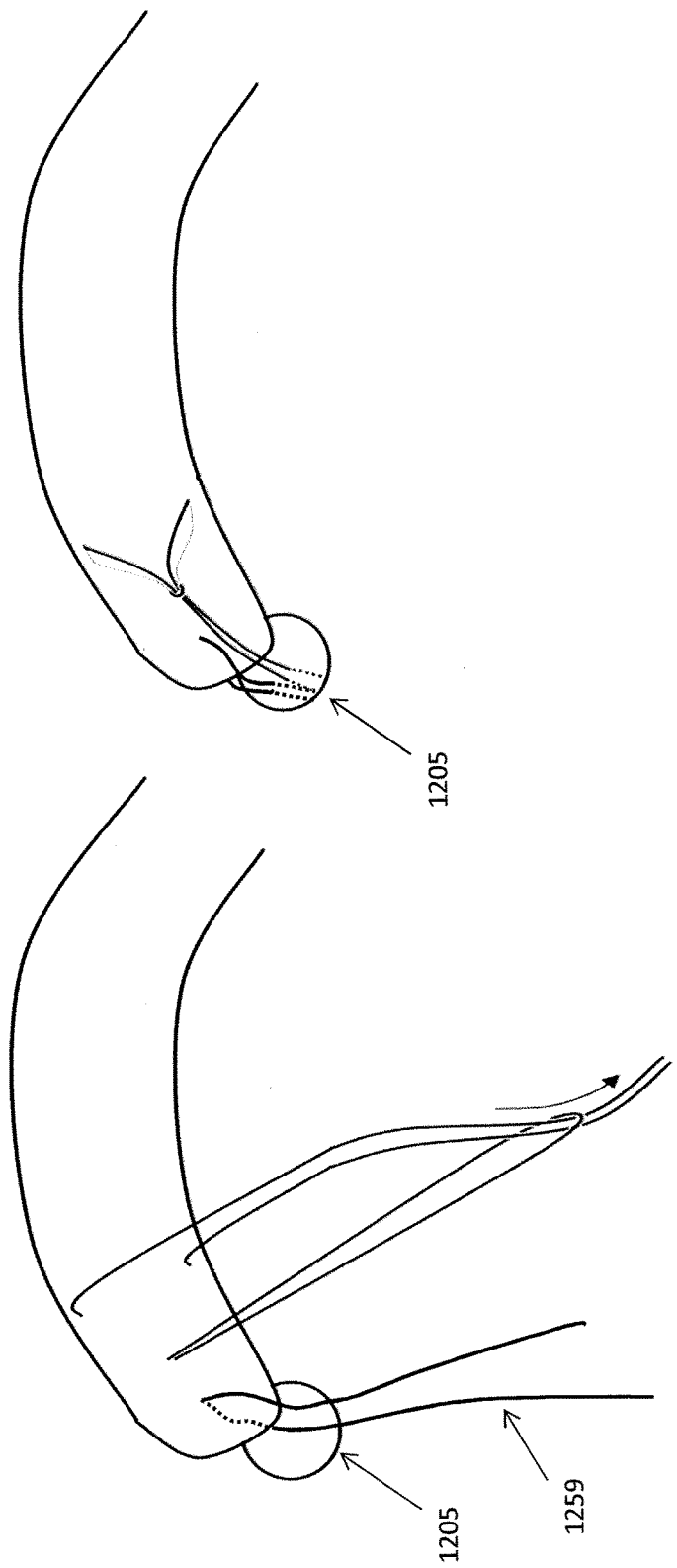
FIG. 13H Simple stitch 2 and locking loop
FIG. 13I All suture limbs pulled down into trough Pass loop leaving ample suture outside the knee Pass one limb through peripheral section of meniscus more towards mid-body than first Pass second limb through central part of meniscus in the same angular position as the first limb Pull ends of suture through loop and then into tunnel

TRANSOSTEAL ANCHORING METHODS FOR TISSUE REPAIR

CROSS REFERENCE TO RELATED APPLICATIONS

This patent application claims priority to U.S. provisional patent application No. 61/862,414, filed Aug. 5, 2013, and titled "TRANSOSTEAL ANCHORING METHODS FOR TISSUE REPAIR" which is herein incorporated by reference in its entirety.

This patent application also claims priority as a continuation-in-part of U.S. patent application Ser. No. 13/893,209, filed May 13, 2013, and titled "IMPLANT AND METHOD FOR REPAIR OF THE ANTERIOR CRUCIATE LIGAMENT", now U.S. Pat. No. 8,888,848, which claims priority as a continuation of U.S. patent application Ser. No. 13/347,184, filed Jan. 10, 2012, and titled "IMPLANT AND METHOD FOR REPAIR OF THE ANTERIOR CRUCIATE LIGAMENT", now U.S. Pat. No. 8,500,809, which claims priority to U.S. Provisional Patent Application No. 61/431,293, filed Jan. 10, 2011, and titled "IMPLANT AND METHOD FOR REPAIR OF THE ANTERIOR CRUCIATE LIGAMENT." Each of these patents and patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

In particular, the following patent applications are herein incorporated by reference in their entirety: U.S. patent application Ser. No. 11/773,388, filed Jul. 3, 2007, titled "METHODS AND DEVICES FOR CONTINUOUS SUTURE PASSING," Publication No. US-2009-0012538-A1; U.S. patent application Ser. No. 12/291,159, filed Nov. 5, 2008, titled "SUTURE PASSING INSTRUMENT AND METHOD," Publication No. US-2010-0331863-A2; U.S. patent application Ser. No. 12/620,029, filed Nov. 17, 2009, titled "METHODS OF SUTURING AND REPAIRING TISSUE USING A CONTINUOUS SUTURE PASSER DEVICE," Publication No. US-2010-0130990-A1; and U.S. patent application Ser. No. 12/942,803, filed Nov. 9, 2010, titled "DEVICES, SYSTEMS AND METHODS FOR MENISCUS REPAIR," now U.S. Pat. No. 8,562,631.

FIELD

This invention relates to methods and apparatuses (including devices and systems, as well as devices and systems for performing the methods described herein) for repair of tissue by anchoring the tissue to or within a bone using an anchor that is inserted almost completely through a bone before being anchored in place. In particular, described herein are methods and apparatus for repair of the anterior cruciate ligament (ACL).

BACKGROUND

Tears to the anterior cruciate ligament (ACL) are painful and often debilitating. Surgery for ACL injuries typically involves reconstructing the ACL using a graft material to replace the torn ACL. For example, ACL reconstruction surgery typically uses a graft to replace or support the torn ligament. The most common grafts are autografts from the patient (e.g., from a tendon of the kneecap or one of the hamstring tendons), though donor allograft tissue may also be used, as well as synthetic graft material. Although ACL reconstruction surgery is often referred to as ACL "repair" surgery, the current standard of care for ACL tears is to replace the torn ligament with a graft, rather than attempting to sew the torn ACL together. Merely sewing together the torn ACL has proven ineffective.

In general, ACL surgery may be performed by making small incisions in the knee and inserting instruments for surgery through these incisions (arthroscopic surgery) or by cutting a large incision in the knee (open surgery). During arthroscopic ACL reconstruction, the surgeon may make several small incisions around the knee. Sterile saline solution is pumped into the knee through one incision to expand it and to wash blood from the area. This allows the doctor to see the knee structures more clearly. The surgeon then inserts an arthroscope into one of the other incisions with a camera at the end of the arthroscope that transmits images of the internal region. Surgical drills may be inserted through other small incisions to drill small holes into the upper and lower leg bones where these bones come close together at the knee joint. The holes form tunnels through which the graft will be anchored. The surgeon may take an autograft at this point. The graft may also be taken from a deceased donor (allograft). In most prior art procedures, a graft may then be pulled through the two tunnels that were drilled in the upper and lower leg bones. The surgeon may secure the graft with screws or staples and close the incisions with stitches or tape.

Unfortunately, replacing the ACL with a graft material, which requires anchoring both ends of the graft material to bone, has proven technically difficult, resulting in a long surgical time, and may ultimately require a long recovery time. Replacement of native ACL material with graft material typically leads to the loss of native ACL proprioceptive fibers, and results in an alteration of the native ACL tibial footprint geometry. In some cases, removing autograft material from the patient may result in donor site morbidity, while donor allograft material presents an increased risk of HIV and Hepatitis C transmission.

In addition, anchoring tissue to bone, both in ACL procedure and more generally, has proven challenging. For example, anchoring tissue to bone in regions of limited access, such as the joints (e.g., knee, shoulder, hip, etc.) without having to displace, and potentially further damage, the joints has proven difficult. Access to the bone attachment site may be difficult in the confined region of the joint, making it particularly difficult to manipulate and secure an anchor within this region. One possible solution has been drill one or more passages through the bone from outside of the joint to form an opening in the joint space, and then anchor the tissue from the outside of the confined joint region, for example, by pulling the tissue, graft and/or suture through the bone passage to the opposite side of the bone. Unfortunately, this procedure results in poor fixation, as the tissue, graft and/or suture may stretch over time.

Thus, it would be desirable to provide devices, systems and methods for repair of the ACL that do not require the replacement of the ACL and the formation of multiple anchoring sites. The apparatuses (systems and devices) and methods for repair of the ACL described herein may address these concerns.

SUMMARY OF THE DISCLOSURE

The present invention relates to apparatuses and methods for repair of tissue (including, but not limited to ACL) using an anchor that may be passed through a tunnel from a first opening on a first side of the bone channel to an opposite side of the bone tunnel. The anchor may be used with a graft material that may be sutured directly onto the torn tissue. The systems and methods described herein may use a suture passer configured to operate in the narrow confines of a bone joint, including those having independently operable sliding and bending jaws with a completely retractable tissue penetrator, such as those described in many of the applications previously incorporated by reference in their entirety, including at least: U.S. patent application Ser. No. 11/773,388, filed Jul. 3, 2007, titled "METHODS AND DEVICES FOR CONTINUOUS SUTURE PASSING," Publication No. US-2009-0012538-A1; U.S. patent application Ser. No. 12/291,159, filed Nov. 5, 2008, titled "SUTURE PASSING INSTRUMENT AND METHOD," Publication No. US-2010-0331863-A2; U.S. patent application Ser. No. 12/620,029, filed Nov. 17, 2009, titled "METHODS OF SUTURING AND REPAIRING TISSUE USING A CONTINUOUS SUTURE PASSER DEVICE," Publication No. US-2010-0130990-A1; and U.S. patent application Ser. No. 12/942,803, filed Nov. 9, 2010, titled "DEVICES, SYSTEMS AND METHODS FOR MENISCUS REPAIR," now U.S. Pat. No. 8,562,631; U.S. patent application Ser. No. 13/462,773, filed May 2, 2012, titled "SUTURE PASSER DEVICES AND METHODS," now U.S. Pat. No. 8,465,505; and U.S. patent application Ser. No. 13/323,391, filed Dec. 12, 2011, titled "SUTURE PASSER DEVICES AND METHODS," Publication No. US-2012-0283753-A1.

Although the methods and apparatuses described herein may be used to repair a torn anterior cruciate ligament (ACL), these methods and apparatuses are not limited to ACL repair, but may be generally applicable and used to repair tissue, and particularly tissue within a constricted region of the body (including joints) that would benefit from attachment to a bone. Thus, although the examples described herein illustrate ACL repair, it should be understood that any tissue, graft, or implant may be repaired using these methods and apparatuses. For example, repair of torn ligaments in the shoulder, hip, spine, or the like, including, without limitation, repair of the rotator cuff repair.

In general, the methods described herein may be referred to as transosteal because they may include the step of forming a passage, channel, tunnel, or the like (which may be referred to as a "tunnel" for convenience) through a bone (such as, for example, a femur head) from a first side of the bone to a second side of the bone, and passing an anchor through the tunnel from either the first side or the second side and all the way through the bone passage to the opposite side where it is anchored in place. The suture may be cinched in the anchor by pulling from the first side of the bone when the anchor is located on the second side of the bone. The bone anchor may be adapted for both passing through the tunnel and for anchoring into the bone after passing through the tunnel. The bone anchor may be referred to as a transosteal bone anchor (and/or suture anchor). A transosteal bone anchor may include a passageway through the anchor (e.g., along the length of the anchor) so that a suture, graft, and/or tissue may be pulled through the anchor and cinched in place. Thus, the suture anchor may include one or more locking elements (e.g., one-way locks) to permit suture, graft and/or tissue to be drawn into the anchor, but prevent the suture, graft and/or tissue from exiting the anchor.

For example, described herein are methods for transosteally repairing a tissue that include the steps of: forming a tunnel through a bone so that the tunnel extends from a first side of the bone to a second side of the bone; passing a suture anchor through the tunnel from the first side of the bone, through the tunnel and adjacent to the second side of the bone; securing the suture anchor within the tunnel adjacent to the second side of the bone; securing a torn end of the tissue to a suture; and cinching the suture in the suture anchor by pulling the suture through the anchor from the second side of the bone and out of the first side of the bone.

The method may also include securing the torn end of the tissue to a graft coupled to the anchor.

In some variations, forming a tunnel comprises drilling an elongate, straight tunnel through the bone. The tunnel may include a first opening (into the bone) on the first side of the bone, and a second opening (into the bone) on a second side of the bone. In general, the tunnel is straight, however the tunnel may also be curved. The anchor and tunnel may be configured to complement each other, so that the suture anchor may be configured for transit through the tunnel from a first side of the bone to the second (opposite) side of the bone. The tunnel and/or anchor may be sized and configured so that the anchor may pass through the tunnel until reaching the second side of the bone, wherein the anchor may be secured in position. For example, the tunnel may be tapered or may include a smaller second opening than first opening.

Any of the methods or apparatuses described herein may include a transosteal bone anchor that includes one or more elements to help the anchor stay fixed at or near the second end of the tunnel. For example, the anchor may be threaded or may include one or more projecting members that are configured to project from the anchor and engage the wall or walls of the tunnel. In some variations the wall of the tunnel may be adapted to receive one or more members from the anchor. For example, the wall of the tunnel may include an indentation, cavity, notch, or the like to receive a extending member from the anchor once the anchor is in position; the extending member from the anchor may be biased to open when the anchor is in position, pushing (extending) the extending members into the receiving region(s) and preventing the anchor from moving within the tunnel once in position. For example, securing the suture anchor within the tunnel adjacent to the second side of the bone may comprise extending one or more locking arms from the suture anchor once it has been positioned adjacent to the second side of the bone.

In some variations, the anchor is advanced in the tunnel and/or secured in the tunnel by screwing the anchor into the tunnel. In some variations, the tunnel may be threaded over all or a portion of its length (e.g., all except the portion near the second side of the bone.

In general, the tunnel may be formed by drilling. For example, forming a tunnel may comprise drilling an elongate, straight tunnel through the bone from the first side of the bone to the second side of the bone. In some variations the method may be performed with a guidewire. The guidewire may be used to form the tunnel and/or to place the anchor, and/or to draw the suture through the anchor and/or tunnel. For example, forming a tunnel may comprise driving a guidewire through the bone from the first side of the bone to the second side of the bone. The guidewire may be a needle or rigid wire. The guidewire may couple or connect to a suture and/or anchor.

In some variations, passing a suture anchor may comprises passing a suture anchor having a central passageway configured to permit a suture to be pulled in a first direction while preventing the suture from being pulled in a second direction that is opposite to the first direction.

In some variations, securing the suture anchor within the tunnel adjacent to the second side of the bone comprises securing the suture anchor within the tunnel so that a distal end of the suture anchor extends from the second side of the bone; alternatively, the suture anchor may be secured so that the suture anchor is recessed within the tunnel relative to the second side of the bone; alternatively, the suture anchor may be secured so that an end of the suture anchor is flush with the second side of the bone.

The step of securing a torn end of the tissue to a suture may comprise percutaneously suturing the torn end of the tissue with a suture passer near the second side of the bone. In general, a suture passer such as those discussed and described herein may be used to percutaneously suture the torn tissue. For example, a suture passer may be configured with a first jaw that is slideable relative to the second jaw, and the second jaw may be hinged to pivot relative to the first jaw and/or the elongate body of the suture passer. In a retracted configuration, with the first jaw retracted proximally relative to (and/or into) the elongate body of the suture passer, the second jaw may be angled to allow a high degree of maneuverability within a confined tissue region such as a joint that is at least partially surrounded by bone. The first jaw member may be extended after placing the second jaw adjacent to the target tissue, so that the first and second jaws may form an open, distal-facing mouth around the target tissue to pass a suture between the first and second jaws.

In general, the suture, and particularly the end of the suture extending from the anchor toward the first side of the bone, may be trimmed or cut. The thus, in some variations, the method may comprise cutting the end of the suture extending from the first side of the bone.

In general, the tunnel through the bone may be filled and/or closed off after cinching and securing the torn tissue (e.g., ligament) in or to the bone. For example, any of the methods described herein may include a step of filling the tunnel through the bone after cinching the suture in the anchor. The tunnel may be filled with bone cement (e.g., poly methyl methacrylate), and/or bone chips, or the like.

Also described herein are methods of repairing torn anterior cruciate ligaments (ACL). For example, described herein are methods for the transosteal repairing a torn anterior cruciate ligament (ACL), the method comprising: forming a tunnel through a femur so that the tunnel extends from a first side of the femur to a second side of the femur; passing a suture anchor through the tunnel from the first side of the femur, through the tunnel and securing the suture anchor near the second side of the femur; securing a torn end of the ACL to a suture; and anchoring the suture in the suture anchor by pulling the suture through the anchor from the second side of the femur and out of the first side of the femur, wherein the anchor comprises a one-way lock configured to prevent the suture from pulling out of the anchor toward the second side of the femur.

Also described herein are methods for transosteally repairing an anterior cruciate ligament (ACL) within the femoral notch, the method comprising: forming a tunnel through a femur so that the tunnel extends from a first side of the femur to a second side of the femur within the femoral notch; anchoring a suture anchor within the tunnel and adjacent to the second side of the femur; securing the suture anchor within the tunnel adjacent to the second side of the femur; securing a torn end of the ACL to a suture; and cinching the suture in the suture anchor by pulling the suture through the anchor from the second side of the femur and out of the first side of the femur, wherein the anchor comprises a one-way lock configured to prevent the suture from pulling out of the anchor toward the second side of the femur.

For example, described herein are methods for repairing a torn ACL within the femoral notch. In some variations, the methods include the steps of: anchoring a graft within the femoral notch; and suturing a torn end of the ACL to the graft within the femoral notch. In general, the step of anchoring the torn end of the ACL to the graft is performed percutaneously. The graft may be integral to (or pre-attached to) an anchor such as a knotless anchor. In some variations the torn end of the ACL is twice anchored within the femoral arch: both to a suture passed through and/or around the torn end of the ACL, and then to a graft that is anchored within the ACL. The connection to the graft may be made second, so that it may reinforce the suture which can be secured within the ACL to the same (or in some variations a different) bone anchor.

For example, in some variations, the step of anchoring a graft comprises securing an anchor to which a graft has been coupled within the femur so that a proximal end of the graft extends from the femur. For example, anchoring a graft may comprise driving a guidewire through the femur and drilling an opening to hold a graft anchor; and securing an anchor coupled to a graft within the opening over the guidewire.

The anchor may be secured by screwing the anchor into the opening (e.g., the tunnel drilled through a region of the femoral notch).

In some variations, the method includes securing the torn end of the ACL to a suture and pulling the suture through the femur to position the torn end of the ACL adjacent to the graft. The step of suturing the torn end of the ACL may comprise passing a suture through the graft and the ACL multiple times, e.g., with a suture passer that is adapted for use within the narrow confines of the tissue. For example, the step of suturing the torn end of the ACL may comprise passing a suture through the graft and the ACL multiple times with a continuous suture passer without removing the suture passer from the tissue.

In some variations the method further comprises securing the torn end of the ACL to a suture and pulling the suture through the femur to anatomically tension the ACL adjacent to the graft.

Also described herein are methods for repairing a torn ACL within the femoral notch, the method comprising: anchoring a graft within the femoral notch; positioning a torn end of the ACL adjacent to the graft; and percutaneously suturing the torn end of the ACL to the graft within the femoral notch.

In some variations, the step of positioning comprises securing a suture to the torn end of the ACL. For example, pulling the suture through a tunnel in the femoral notch to position the torn end of the ACL adjacent to the graft. In some variations, the method includes the step of anchoring the torn end of the ACL to the femoral notch with a suture before percutaneously suturing the torn end of the ACL to the graft.

In any of the variations of methods described herein, the method may include forming (e.g., drilling) a tunnel through the femoral arch for anchoring the torn ACL. The step of anchoring the graft within the femoral notch may include anchoring the graft within a tunnel drilled through the femoral arch.

Also described herein are methods for repairing a torn ACL within the femoral notch, the method comprising: drilling a tunnel through a portion of the femoral notch; anchoring a graft within the tunnel through the femoral notch, wherein the graft extends from the tunnel; pulling a suture connected to a torn end of the ACL through the tunnel through the femoral arch to positioning the torn end of the ACL adjacent to the graft; anchoring the suture connected to the torn end of the ACL; and percutaneously suturing the torn end of the ACL to the graft within the femoral notch.

BRIEF DESCRIPTION OF THE DRAWINGS

FIG. 6 shows another variation of a knotless ACL repair screw.

FIGS. 7A and 7B show another variation of a knotless ACL repair anchor.

FIGS. 13A-13E show one variation of meniscal root repair using a double locking loop stitch.

FIGS. 13F and 13G illustrate an alternative method of securing tissue (e.g., meniscal root) in which a simple stitch is used as well as a locking loop stitch to secure the tissue.

FIGS. 13H and 13I show another variation of a method of securing tissue (e.g., meniscal root) in which a simple stitch is used with a locking loop to secure the tissue.

DETAILED DESCRIPTION

Figure 1A:
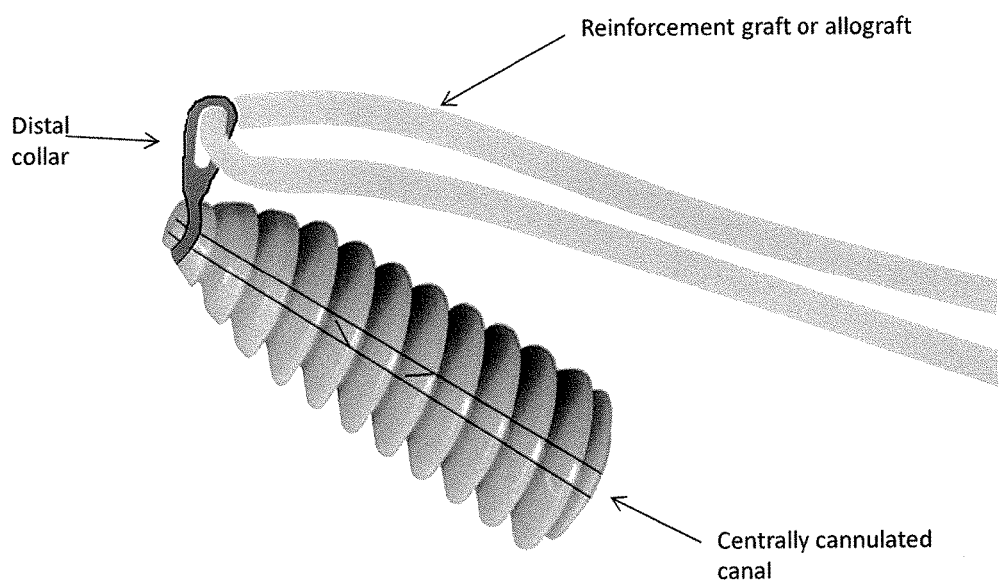
FIGS. 1A and 1B show one variation of a knotless ACL repair screw (anchor) as described herein.

In general, described herein are methods and apparatuses for repairing a torn tissue, including transosteal methods of repairing a torn tissue. These methods may include the steps of forming a channel through a bone that extends from a first side of the bone to an opposite (second) side of the bone, securing an anchor in the tunnel at or near the second side of the tunnel, percutaneously suturing the torn tissue to secure the suture to the torn end of the tissue, and pulling the suture and torn tissue toward the anchor, though an opening in the anchor and/or tunnel from the second end of the tunnel toward the first end of the tunnel, thereby securing the suture and/or tissue within the bone tunnel and/or anchor. In particular, these methods may include securing the anchor by passing the anchor though the tunnel from the first side of the bone to (or near) the second side of the bone. This method may allow minimally invasive repair of torn tissue and/or implantation of grafts or other materials, even in very narrow or confining spaces such as bone joints, without having to distend or otherwise open up the space and potentially damage the surrounding tissue, as is currently required in many tissue repairs.

For example, described herein are methods and devices for use in repair of a patient's anterior cruciate ligament (ACL). These methods (and devices for performing them) allow the repair, rather than merely replacement, of the ACL. As discussed above, although the ACL is used to exemplify the apparatus and methods of the present invention, these apparatuses (devices and systems) may also be used with many other tissues and are not limited to the repair and/or replacement of ACL tissue.

The anchoring devices described herein may be inserted into a bone and may hold a graft material within the bone so that the graft may also be attached to the torn or damaged ACL. The implanted anchoring device (which may also be referred to as an "implant" or "knotless graft anchor" or "suture anchor") may be particularly well suited for use with any of the low-profile and/or continuous suture passers described herein, since these suture passers may allow access to previously inaccessible regions of the knee (or other body regions). For example, the methods described herein may include access into the notch region (e.g., the femoral notch) to anchor a graft in an optimal position, and to suture the graft to the damaged ACL while maintaining as much of the native ACL as possible. Previous methods of "repairing" (rather than replacing) the ACL have proven unsuccessful at least in part because this region was difficult or impossible to successfully access. Suturing in the notch region, without the benefit of the continuous suture passers described and incorporated by reference herein, has proven extremely difficult and time consuming, discouraging such surgical repairs.

In variations including a graft material, any appropriate graft material may be used. For example, an ACL graft for use with the methods and devices described herein may include: synthetic grafts (e.g., Gore-Tex, Dacron, carbon fibers, and polypropylene braids, etc.), biologic (e.g., porcine, human or other) allografts, autografts, etc. The graft materials describe herein may provide support or scaffolding for repair of the torn ACL, since the ACL is left in place and sutured to the graft. Thus, in some variations the graft may be a sleeve or patch (e.g., a graft jacket, Restore patch, etc.) The graft may include a biologic material such as a growthpromoting material that may promote in-growth, visualization, or the like (e.g., growth factors, etc.).

In general, the apparatuses (e.g., devices and/or systems) described herein may include a knotless anchor, such as a knotless ACL graft anchor, which may also be referred to as an ACL graft anchor, a one-way ACL graft anchor, a knotless ACL repair screw, or merely a "device" in the description below. These ACL graft anchors are one type of anchor that may be used, and (like other types of anchors) may include a one-way path for passing (and therefore anchoring) a suture. The ACL graft anchor may also include a coupling region for coupling to a graft material. Any of the anchors that may be used for the procedures described herein (including, but not limited to, the ACL anchors) may include a one-way path may be a central passage through the device. In general a one-way path forms a channel through the device and may include cams or other locking members that prevent a suture passing through the one-way path from pulling out the device. The one-way path may be referred to as the suture channel or path, since the suture may extend through (and be held within) the one-way path, although other elements (e.g., a guidewire, such as a beath pin, etc.) may also be passed through the channel. The one-way channel may extend from the proximal to the distal ends of the device, which may advantageously allow the anchor to be easily implanted and positioned, and may anchor the suture (e.g., connected to an ACL) at or within a bone region of the femoral notch. For example, the suture may be drawn through the implant to pull the distal end portion of a torn ACL towards (and to or into) the proximal end of the anchor. The anterior end of the implant is typically the end that faces the torn tissue, and may not be completely inserted into the bone, and may face away from the bone.

As mentioned above, some variations of the anchors described herein allow both securing (e.g., suturing) of the torn ACL to the scaffold/support (e.g., graft) after the graft has been anchored into the bone, and also tensioning of the torn ACL by pulling and locking the position of a suture that has been secured to the torn end of the ACL. In particular, the anchor includes a one-way pathway that allows the suture connected to the torn end of the ACL to be pulled and held (locked) distally, to adjust the tension on the ACL as it is being positioned adjacent to the graft so that it can then be sutured to the graft. The one-way locking mechanism in the suture pathway through the anchor allows this tensioning. Thereafter, the reinforcing support of the graft (scaffolding) maintains the tension and position of the ACL for short-term repair and long-term healing. Thus, described herein are anchor devices that are configured to both pre-tension a torn ACL and to secure the tensioned ACL to the reinforcement graft anchored in the bone by the device. Some variations of these devices therefore may include a one-way (locking) path for a suture to be drawn through the body of the anchor as well as a coupling region for a graft, or a graft that is already integrally part of the device.

The coupling region that may couple to a graft may be located as the distal end (e.g., the end to be inserted into the bone) of the device so that the graft will be anchored at one end in the bone. The coupling region may be positionable or rotatable around the circumference of the device. In some variations the coupling region is a loop or ring that is rotatably attached around the distal end region of the ACL anchor, which is also connected to a second loop or ring through which the graft (e.g., ACL graft) may pass and be secured. A coupling region may be referred to as a collar. Alternatively, the attachment region may include a suturing substrate (e.g. fabric) to which the graft may be coupled or connected. In some variations, the coupling region may include a passage through the device through which the graft may be passed. In some variations the coupling region is connected (or formed of) the distal end of the ACL anchor, which may be rotatable around the long axis of the ACL graft anchor.

Thus, in general, the ACL anchors described herein are configured to secure both an ACL graft (which is to be sutured to the ACL) and a suture that is also connected to the torn ACL.

The ACL anchors described herein may also be configured to secure within an opening drilled into the bone (e.g., a tunnel into the bone, as shown in the figures and discussed below). The sides of the anchor may be self-tamping, ridged, expandable, or the like, to secure the anchor within the bone. The body of the anchor may also include one or more passages or opening into which bone may grow (or be encouraged to grow). In some variations the device includes lateral openings into which a cross-pin or other additional anchoring device may be inserted.

Figure 1B:
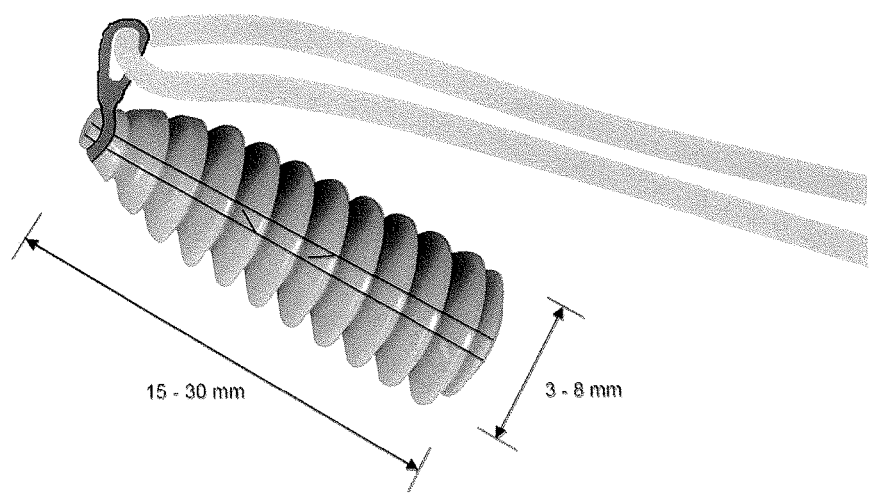

For example, FIGS. 1A and 1B show one variation of an anchor, configured as a knotless ACL repair screw (ACL graft anchor). In this example the ACL graft anchor has a screw-shape body (e.g., a threaded body) that extend in a proximal-distal longitudinal direction. The distal end includes a distal collar for attachment to a graft material; the distal collar (coupling region) includes a loop through which the graft material may pass and be secured, and a collar region surrounding an opening at the distal end. Thus, the collar can rotate relative to the body of the device. This allows the threaded, screw-shaped body to be screwed (rotated) into position within the bone, while the graft at the distal end may remain in the same position (e.g., on one side of the body). In FIG. 1A, the distal collar can rotate freely with respect to the screw (body of the anchor), and has an eyelet through which any reinforcement graft or allograft can be inserted (e.g., a graft jacket, Restore Patch, tibialis anterior allograft, etc.).

Other examples of anchors that may be used may not include the graft attachment region, but may be otherwise similar. For example, the anchor may include threaded sides and a central channel with a one-way locking mechanism for the suture. In some variations it is not necessary to use a graft to secure the torn tissue (e.g., ACL) within the anchor and therefore the bone; the torn tissue may be directly sutured as shown and described below (e.g., FIGS. 4A-4D), and the suture secured to the anchor.

An ACL repair screw (anchor) body such as the one shown in FIG. 1A may be made out of relatively strong and biocompatible material, such as PEEK. In this example, the outer body region is threaded for screwing into a channel made in the bone. The device includes a central channel that creates a one-way passage for a suture, and can thereby anchor a suture in position. For example, the central channel may include tabs that create a one-way pathway for a suture. In other variation the suture is allowed to pass only in one direction (e.g., towards the distal end of the implant) by tabs, clamps, cams, ball valves, check valves, or the like).

FIG. 1B shows the device of FIG. 1A with exemplary range of dimensions (e.g., length of approximately 15-20 mm, and width of approximately 3-8 mm). In some variations, a smaller diameter screw may be beneficial because a smaller diameter screw will allow more contact of the ligament to bone at the repair site.

Figure 1C:
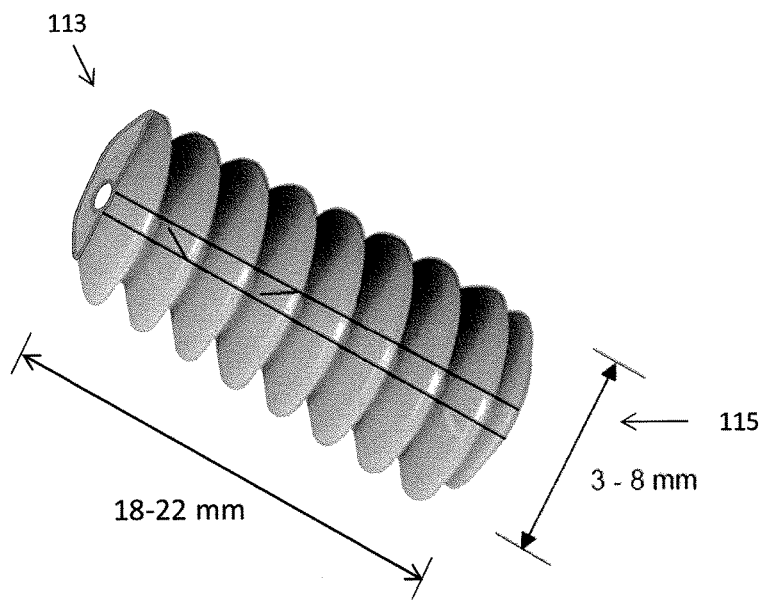
FIG. 1C shows another variation of a knotless anchor that may be used.

FIG. 1C shows another variation of an anchor, similar to the anchor shown in FIGS. 1A-1B, but without the external graft attachment. In this example, the anchor may be screwed into the bone (e.g., into a tunnel formed through the bone). The anchor may include an attachment site (not visible in FIG. 1C) for connecting to an applicator or holder. The attachment site may be located at one end (e.g., the distal end 115) of the anchor and may hold the anchor so that can be screwed into the bone. The attachment site may be internal threading or other releasable attachment. In some variations, as described below, the anchor may be screwed from a first side of the bone into the tunnel drilled through the bone until the anchor; e.g., the proximal end of the anchor 113 may extend slightly from the second bone surface, or it may be flush with the bone surface, or it may be recessed slightly (e.g., a few mm or less) relative to the bone surface.

FIGS. 5 to 7B, 10G-10K and 11B also illustrate alternative variations of anchors that may be used with the systems and methods described herein. For example, in FIG. 5, the anchor includes a central one-way path for a suture that is locked in place by a ball valve. In FIG. 6, the anchor also includes a passageway completely through the anchor, and includes multiple projecting "arms" or tabs (e.g. locking arms) that extend from the anchor body and may be collapsed against the tunnel wall as the anchor is advanced through the tunnel, but the arms may expand outwards when reaching the position near the second wall of the bone; a lip, recess, or other region may be formed in the bone to hold the locking arms in place. The arms may be oriented to prevent the anchor from pulling out (e.g., in the direction of the torn tissue). In some variations the arms may be "released" once the device is positioned within the cavity, so that the anchor may be readily implanted in the bone by driving it down (through) a bone tunnel from an outer wall of the bone to the inner wall of the bone (the wall facing the torn tissue to be repaired).

Figure 4A:
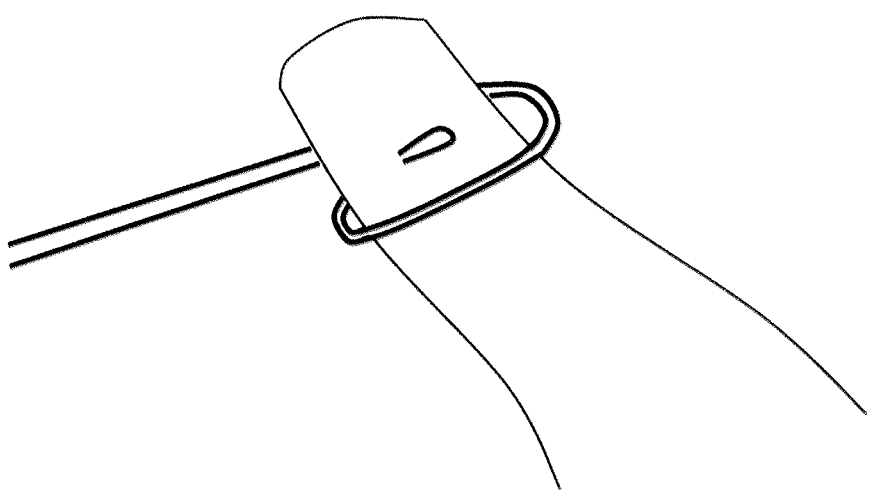
FIGS. 4A-4D illustrate one method of securing an ACL (e.g., a torn ACL) to a suture as described herein.
Figure 4B:
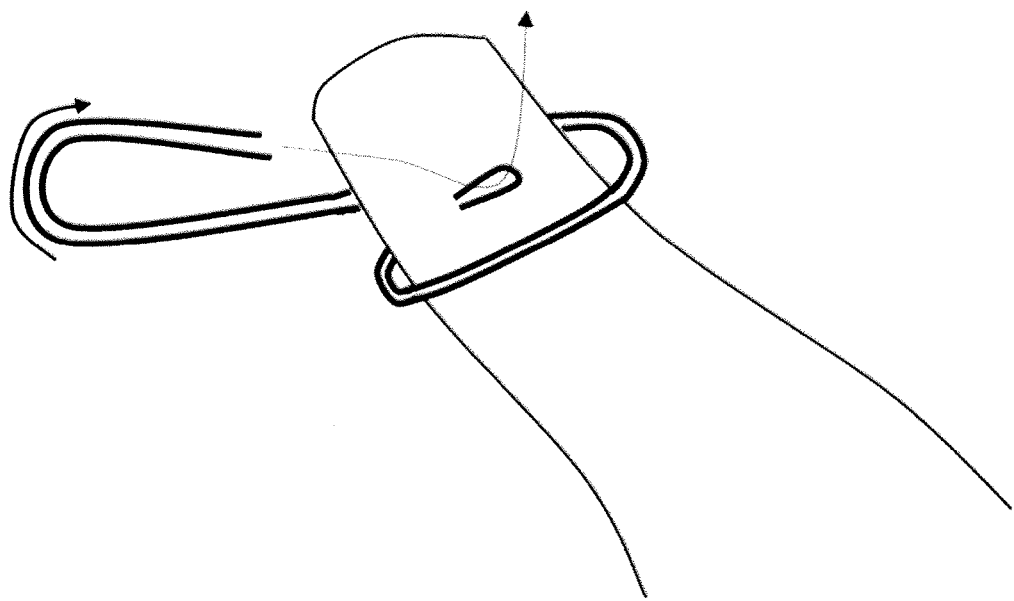
Figure 4C:
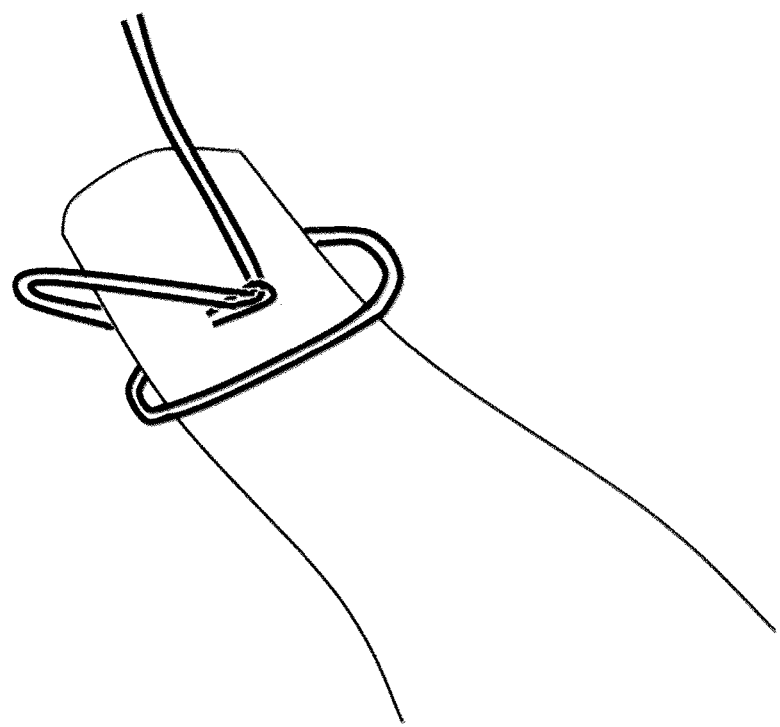
Figure 4D:
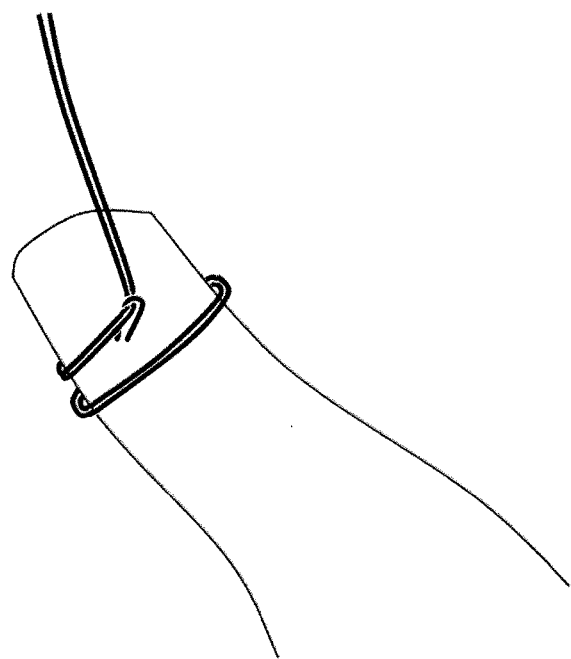
Figure 5:
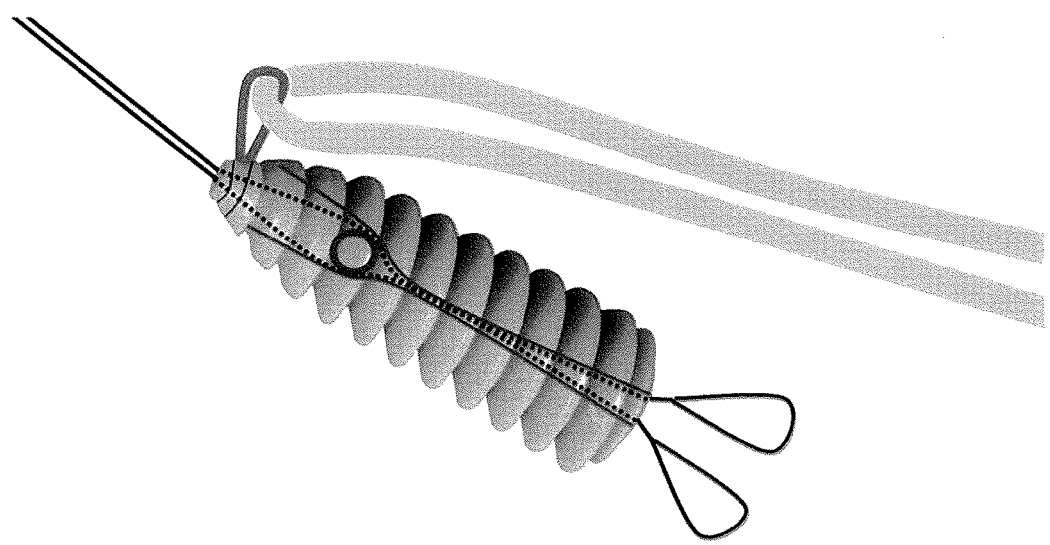
FIG. 5 shows another variation of a knotless ACL repair screw.

A passageway for the suture and/or tissue (and/or graft) through the anchor may also be valved to allow only one-way travel through the device, as shown. In FIG. 5, the embodiment shown includes a suture forming a loop at the distal end, which may be connected to a tissue (e.g. an ACL) so that the tissue may be drawn towards and anchored into position relative to the anchor. FIGS. 4A to 4D, described in greater detail below, illustrate securing the end of a tissue such as an ACL to a suture so that it can be loaded into a knotless anchor.

FIGS. 7A and 7B illustrate another variation of an ACL anchor in which the anchor secured itself into position within a hole or opening in the bone. This design may allow for a smaller hole to be made in the bone (e.g., the bone forming the notch region). In this example, as shown in FIG. 7A, the implant (with a one-way passage) is inserted into a passage in the bone as shown. In this example, the scaffold material (e.g., graft) is not shown, but may be included. Once in position, the anchor may be locked in place by expanding at least a region of the implant. For example, in FIG. 7B, the proximal end of the device expands outwards against the walls of the opening or passage in the bone, locking it in place, as shown. A suture (not shown) may be pulled through the one-way passage in the anchor, to draw the ACL towards the device, and potentially into the bone. The ACL may then be secured in position and so that in-growth can help anchor it in place. In some variations, the anchor includes a cam or camming mechanism that may create a one-way anchor within the channel for the suture.

As mentioned above, any appropriate suture passer may be used, particularly those described in: U.S. patent application Ser. No. 11/773,388, filed Jul. 3, 2007 and titled "METHODS AND DEVICES FOR CONTINUOUS SUTURE PASSING," Publication No. US-2009-0012538-A1; U.S. patent application Ser. No. 12/291,159, filed Nov. 5, 2008 and titled "SUTURE PASSING INSTRUMENT AND METHOD," Publication No. US-2010-0331863-A2; Ser. No. 12/620,029, filed Nov. 17, 2009, titled "METHODS OF SUTURING AND REPAIRING TISSUE USING A CONTINUOUS SUTURE PASSER DEVICE," Publication No. US-2010-0130990-A1." For example, suture passers having a suture shuttle that is configured to clamp to the side of a curved tissue penetrator that can be extended and retracted to pass the suture shuttle (and any attached suture) back and forth between two open/closed jaws or arms are of particular interest. In this example, the suture shuttle may generally include a shuttle body that clamps to the tissue penetrator, and has an extension region ("leash") with a suture attachment region at the end. In this way the suture may be held slightly apart from the tissue penetrator, and not interact directly with the tissue penetrator.

Figure 8A:
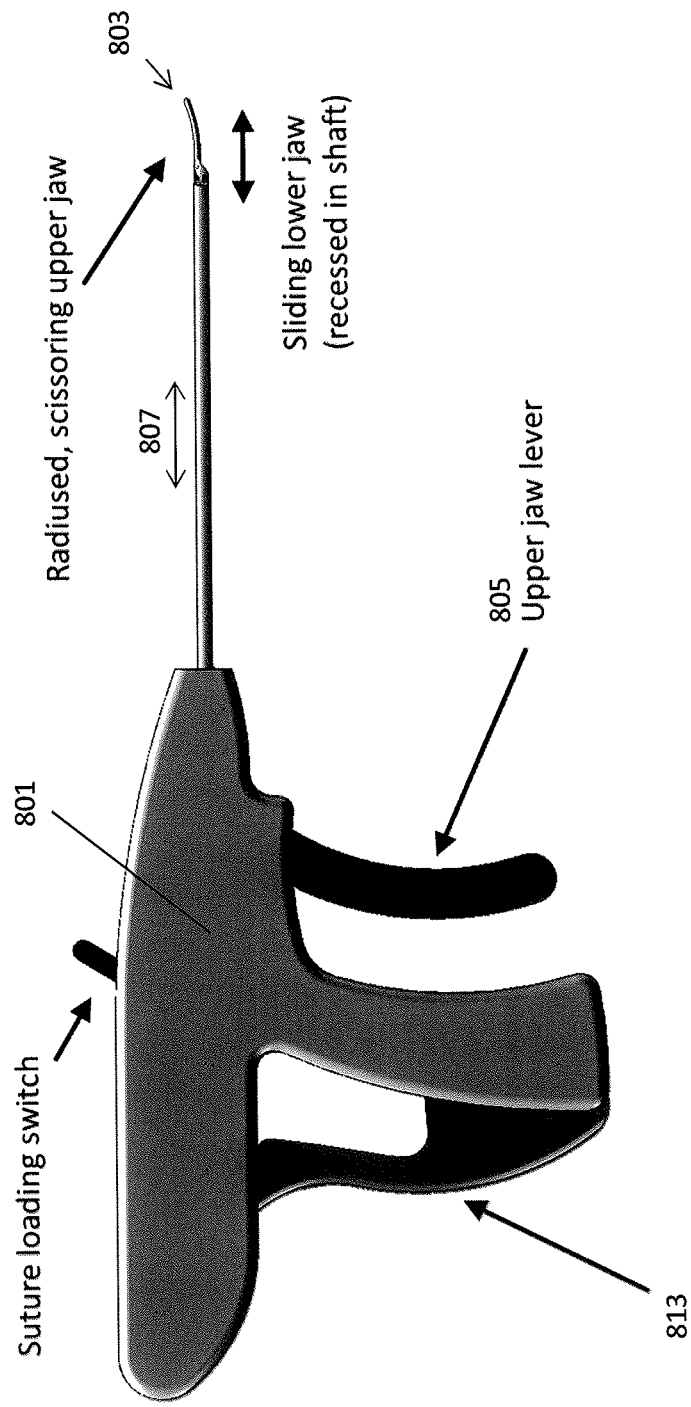
FIG. 8A shows one variation of a suture passer that may be used with the methods and apparatuses described herein. In this example, the lower jaw member is retracted (into the elongate shaft) and the pivoting upper jaw member is bent up at a 30° angle relative to the elongate shaft.
Figure 8B:
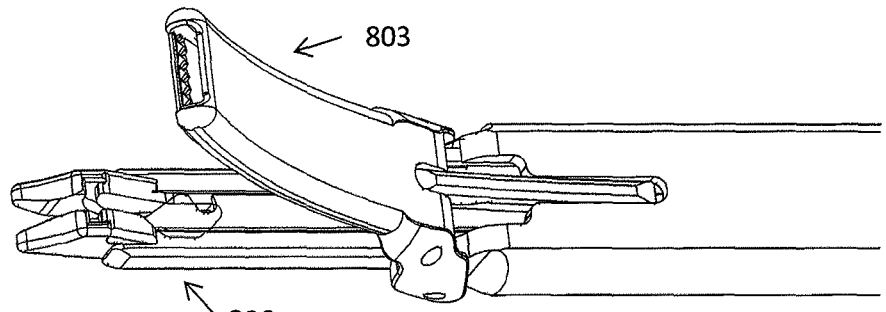
FIGS. 8B and 8C show top perspective and side views, respectively, of the distal end of the suture passer of FIG. 8A; in this example, the lower jaw is fully extended axially to form a distal-facing opening ("mouth") with the pivoting upper jaw. The pivoting upper jaw may pivot relative to the proximal elongate shaft body to which it is connected.

In some variations, the shuttle used for passing the suture by a continuous suture passer may be further adapted for use with the devices and methods described herein. For example, the shuttle may be configured to include a lead wire that allows a region of one or more loop to be cut free after the initial ACL suture is placed (because the central part of the suture may be passed to allow a loop to be formed, through which the proximal aspect of the suture ends can be inserted for a self-cinching pattern. See, for example, FIGS. 4A-4D. FIGS. 8A and 8B illustrate variations of suture shuttles including multiple (two in this example) loops extending from the body of the suture shuttle. The outer loop may be cut away, broken or otherwise opened to release a suture or loop of suture. The same suture shuttle may the then be used again without having to remove it from the tissue, and without having to draw one or both free ends of the suture out of the loop.

Figure 9B:
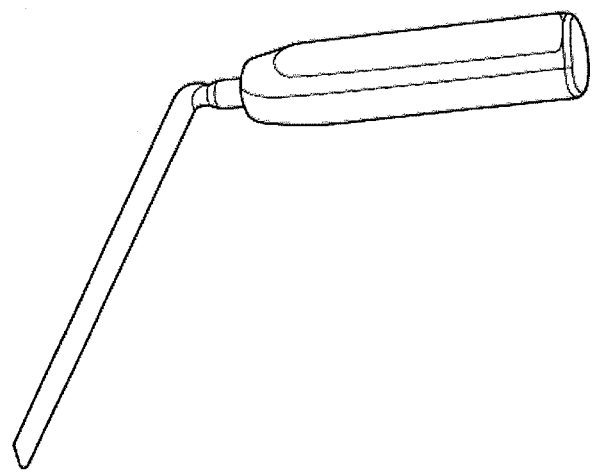
FIGS. 9A and 9B illustrate arthroscopic spatulas that may be used for knot typing and instrument insertion during any of the methods described herein.
Figure 9A:
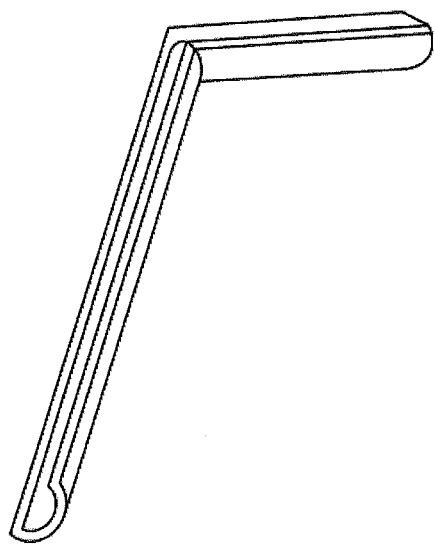

In any of the variations described herein, one or more arthroscopic devices may be used to help manipulate the tissue, in addition to the suture passers (or in place of the suture passers) described. For example, FIGS. 9A and 9B illustrate two variations of arthroscopic spatulas that may be used for knot typing and instrument insertion, as appropriate.

In general, any of the anchors described herein may be used as part of a system for repairing ACL. Such a system may also include a continuous suture passer and or suture material. In particular, continuous suture passers that are capable of passing a suture back and forth (e.g., by connection to a shuttle member) between two arms or jaws while the jaws are open around the tissue (e.g., ACL tissue), are of particular interest. Thus, the system may include the suture passer, and one or more anchors as described herein. For example, the suture passers may include one such as that illustrated in FIG. 8A or 8B.

FIG. 8A-8D illustrates one variation of a suture passer that may be used to secure a suture to a tissue, such as a torn ACL. A suture passer such as the suture passer shown in FIG. 8A may also be adapted to suture tissue using one or more lengths of suture that includes a knot, so that the knot is passed through the tissue by the suture passer.

The suture passer of FIG. 8A has a tissue penetrator that is housed within (with the distal tip within) the lower jaw but, when extended across the distal opening formed between the upper and lower jaw, extends distally from a distal opening in the upper jaw. The tissue penetrator travels in a roughly sigmoidal path from the lower to upper jaw, meaning it is deflected twice: first from the lower jaw to extend across the opening, and then by the upper jaw to extend distally out of the upper jaw. In some variations, two lengths of a suture (including two lengths of the same suture, e.g., two ends of the same suture) can be loaded into the lower jaw and sequentially passed from the lower jaw, through different regions of the tissue and retained in the upper jaw, to pass a length of suture through the tissue. The suture passer show in FIGS. 8A-8D is also configured so that the upper jaw member can pivot to assume a different angle relative to the elongate body of the device, and the lower jaw member is axially extendable distally from the distal end of the elongate member to form a distal-facing mouth with the upper jaw member. The proximal handle includes a plurality of controls for controlling the pivoting of the upper jaw member, the axial sliding of the lower jaw member, and the extension/retraction of the tissue penetrator from the lower jaw member.

For example, FIG. 8A shows the suture passer with the lower jaw fully retracted (relative to the upper jaw) into the elongate shaft. The handle includes controls for operating the upper jaw (pivoting/scissoring), lower jaw (extending/retracting or sliding), and tissue penetrator (passing the suture between the upper and lower jaws). In FIG. 8A, the proximal handle control 805 is configured as a trigger or lever that controls the motion of the upper jaw member ("upper jaw control"). The upper jaw control may be pulled to reduce the angle of the upper jaw relative to the long axis of the elongate member 807. In this variation the upper jaw control is pinned and allowed to drive a tendon in the elongate member distally when compressed to drive the upper jaw down (reducing the angle between the upper jaw and the long axis of the elongate member). This pivoting motion may also be referred to as scissoring (scissoring motion).

A second control 813 ("lower jaw control") is also configured as a lever or trigger, and may be squeezed or otherwise actuated to extend and/or retract the lower jaw 806 to form a distal-facing mouth with the upper jaw, as shown in FIG. 8B. In some variations the lower jaw control is further configured to control deployment of the tissue penetrator 822 to extend and retract across the distal-facing opening 833 formed between the upper and lower jaws. For example, in some variations squeezing the lower jaw control after completely extending the lower jaw may deploy the tissue penetrator from the lower to the upper jaw so that the distal end 825 of the tissue penetrator extends out of the upper jaw. As it extends between the upper and lower jaw, the tissue penetrator may carry a first length (bight) of suture through the tissue. Upon reaching the opposite jaw member, the suture may be removed from the tissue penetrator and held (e.g., by a stripper) in the upper jaw. Upon release of the distal control, the tissue penetrator may withdraw back into the lower jaw. If the user would like to send a second length of suture through the tissue (e.g., after moving the jaws relative to the tissue), actuating (e.g., squeezing) the distal control 813 again may result in the extending the tissue penetrator (along with any second length of suture) back through the tissue from the lower jaw to the upper jaw, where the second length of suture can be retained. Alternately, in some variations, the controls (e.g., to control motion of the upper and/or lower jaw) may be separate from each other, and/or from extending/withdrawing the tissue penetrator. Additional controls may also be included in the proximal handle, include a suture loading control (e.g., switch, toggle, etc.) for loading and/or tensioning the suture within the lower jaw member. In some variations the device includes a release control for releasing the clamp element/suture retainer on the upper jaw. Thus, a loop of material can be left behind in the tissue after withdrawing the suture passer. Alternatively, a loop of suture may be pulled out and through the tissue and the suture manually uncoupled from the upper jaw.

Figure 8C:
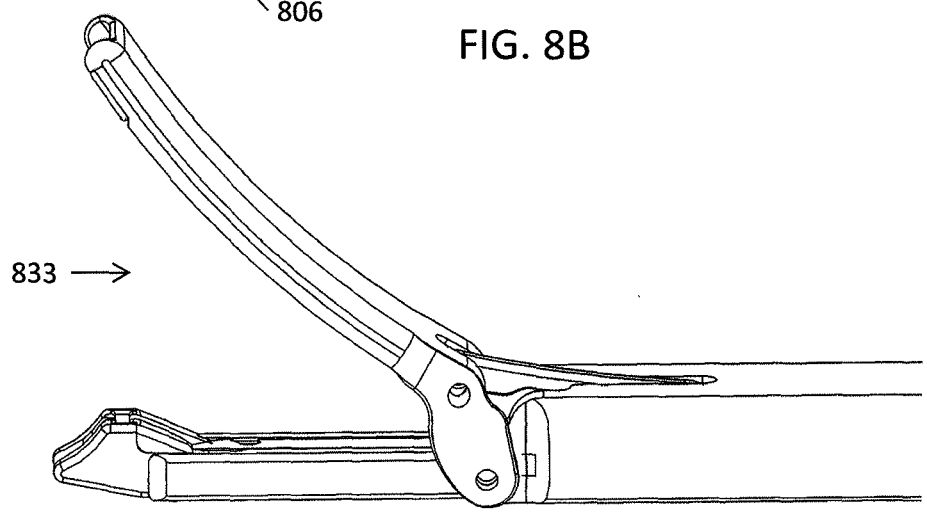
Figure 8D:
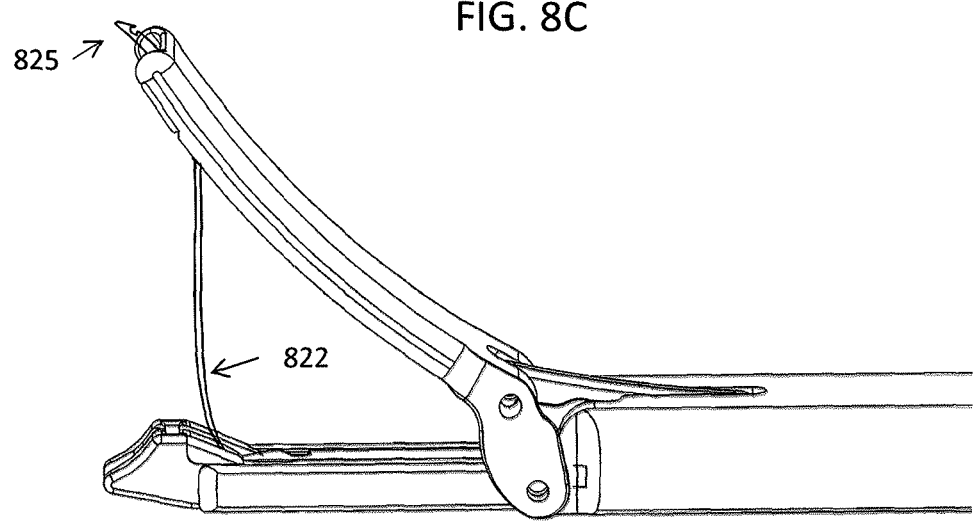
FIG. 8D shows a side view of the distal end of the device of FIGS. 8A-8C, with the tissue penetrator (needle) extended across the distal-facing opening; the tissue penetrator may be used to push and/or pull a suture between the jaws and through tissue held (e.g., clamped) between the upper and lower jaws.

FIGS. 8B-8D show an enlarged view of the distal end of the device of FIG. 8A. For example, in FIGS. 8B and 8C the upper jaw 803 is thin and slightly radiused (e.g., curved), and is hinged to the elongate shaft region of the device. The upper jaw is also connected to a control on the proximal handle by a push/pull member (tendon, wire, rod, etc.), allowing adjustment of the angle of the upper jaw member relative to the elongate member. The upper jaw may also be used to "clamp" tissue to a desired and controllable amount when suturing.

In addition to the suture passers described above, including in FIGS. 8A-8D, the apparatus (e.g., systems) for repairing tissue described herein may also include one or more tools for forming a tunnel, and/or hole or opening in bone into which an anchor may be positioned, and a guidewire, needle or pin that may be useful for inserting the anchor, guiding the formation of the tunnel, and/or for threading a suture through the anchor. Additional manipulation tools, including those shown in FIGS. 9A and 9B, may also be included.

Example 1: Method of Repairing ACL

In set of examples of transosteal methods as described herein are methods of repairing a torn ACL. These methods may include anchoring one end of an anchor (which may include a graft or scaffold) in the femoral notch, for example, by securing an anchor in the femur at the attachment site of the ACL to the bone in the femoral notch. The anchor may hold one end of a flexible scaffold for attaching to the patient's ACL. The scaffold may be a graft, sleeve, patch, or the like. The step of anchoring may include anchoring a scaffold (e.g., graft) using an ACL graft anchor such as those described above. The scaffold may be secured by first driving a pin (e.g., a beath pin) though the posterolateral femoral arch, and drilling an opening into which the ACL graft anchor may sit. In some variations a second tunnel or passage for the graft, adjacent to the first, may also be formed. An ACL graft anchor with an attached ACL scaffold may then be secured into the opening formed through the femoral arch bone. In some variations a guidewire may be used to guide both the drill and/or the anchor so that it can be positioned.

In some variations, as illustrated below, the anchor may be inserted in the desired location by first forming a tunnel through the bone (e.g. femur) and then driving or otherwise pushing the anchor from the outer (first bone) wall which faces away from the torn tissue (e.g., away from the femoral notch) thought the bone in the tunnel so that the anchor is positioned near the inner (second) wall of the bone, facing the femoral notch and the torn ACL tissue. The anchor may be positioned so that it is recessed, flush, or extends slightly from the second wall of the bone in the femoral notch. In variations in which the scaffold (e.g., graft) is attached to the anchor before positioning it in the bone, the graft and anchor may together be driven through the bone tunnel to the second bone wall. For example, the anchor may be adapted to hold the scaffold within a central region or channel of the anchor so that the scaffold can be extended from the anchor for attachment to the tissue once the anchor has been positioned.

In variations using a scaffold, once the scaffold (e.g., graft) is anchored in the femoral arch, the torn end of the ACL, when repairing the torn ACL, may be pulled towards the ACL anchor and scaffold and sutured to the scaffold while in the notch. For example, the end of the torn ACL may be sutured or connected to a suture and the suture drawn though the body of the suture anchor to pull the end of the ACL towards the anchor and the graft. The suture may hold the ACL in position so that it may be sutured (using a separate suture) to the graft material, thereby re-attaching the ACL to the femoral arch region. In some variations the end of the suture is passed through the anchor distally, along the one-way passage through the anchor, holding it in position. This step may be performed to secure the tissue with the anchor even when a graft is not used.

For example, FIGS. 2A-2D illustrate one variation of a method for anchoring a scaffolding (e.g., an ACL graft) and also a method for positioning a torn ACL next to the anchor and graft so that it can be sutured to the graft. Similar steps may be performed even when a scaffold (graft) is not used or connected to the anchor (e.g., the anchor of FIG. 1C). FIGS. 3A-3P show an example of a method for repairing an ACL, including steps for anchoring the scaffolding/support in the femoral notch and suturing the ACL to the scaffolding support while the end of the ACL is in the femoral notch.

Figure 2A:
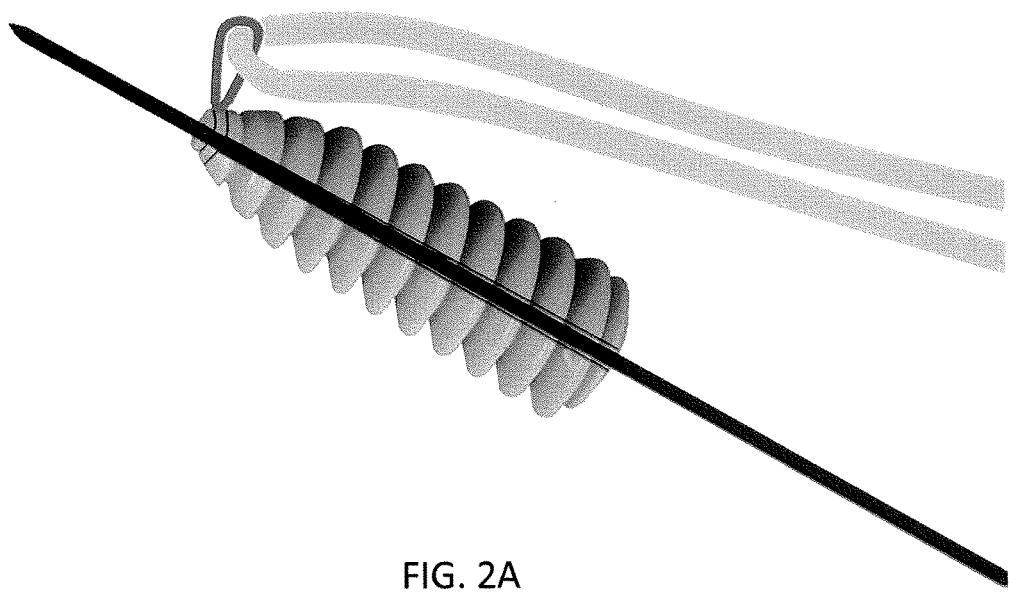
FIGS. 2A-2D illustrate one method of loading a suture into a knotless ACL repair screw such as the variation shown in FIGS. 1A-1B.
Figure 3A:
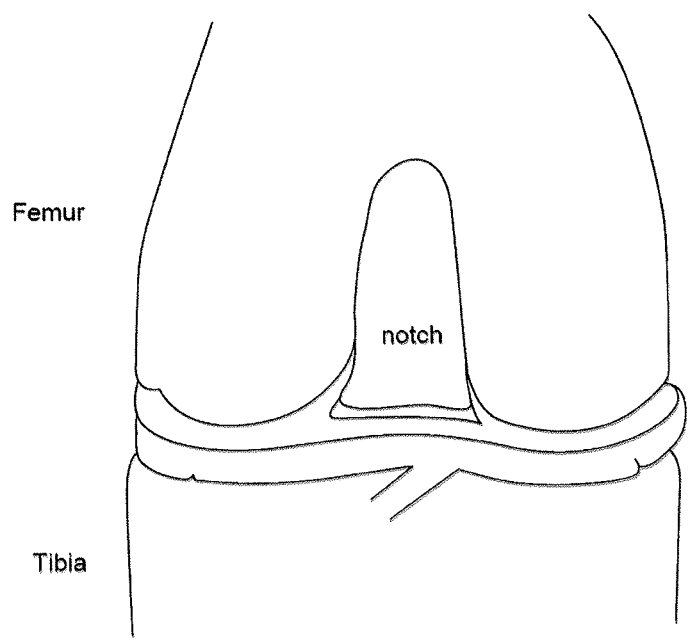
FIGS. 3A-3P illustrate one method of repairing an ACL using a knotless ACL repair screw.
Figure 3D:
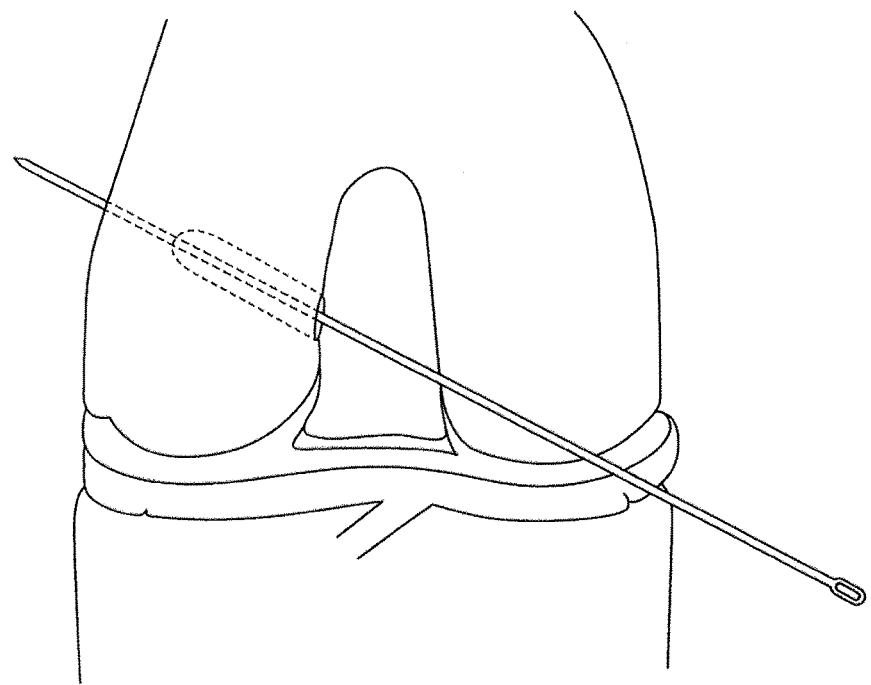
Figure 3E:
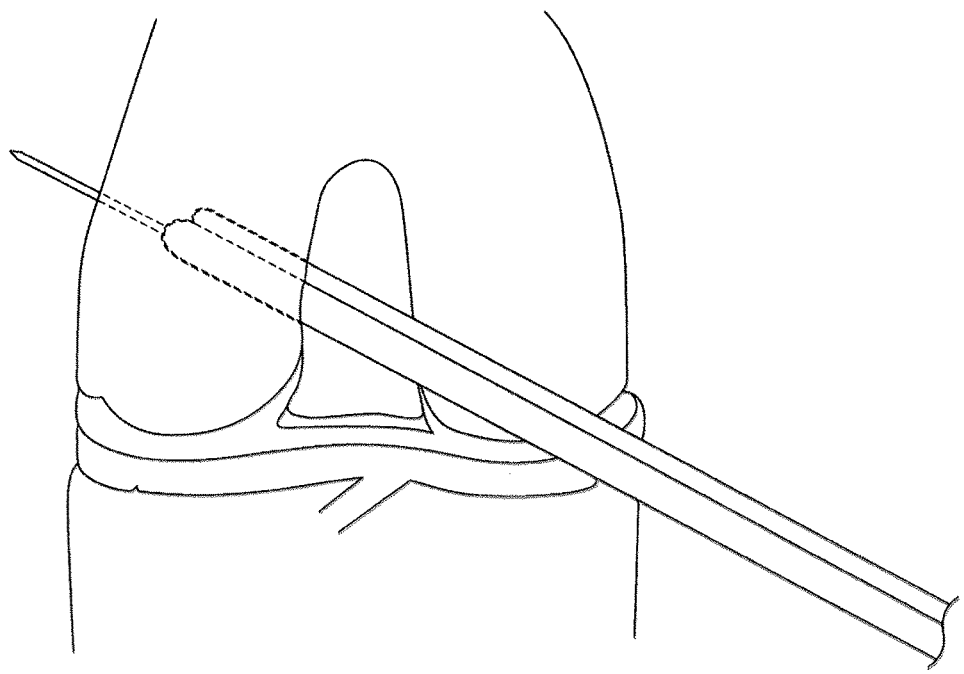
Figure 3F:
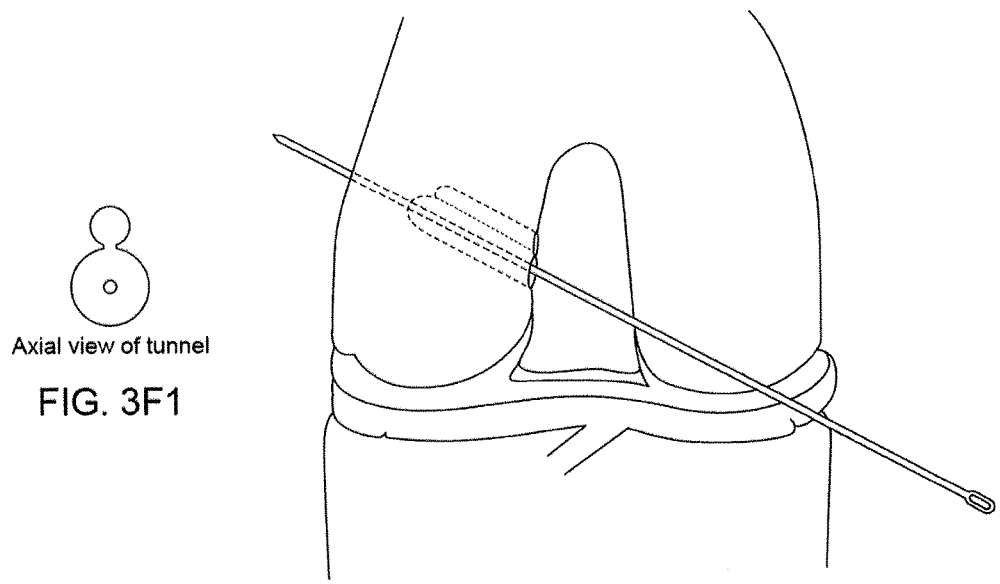

In FIG. 2A, the anchor, which in this embodiment is shown similar to the variation of FIGS. 1A and 1B is an ACL screw anchor, may be threaded over a guide wire. Any appropriate guidewire may be used, for example, a beath pin type of guidewire that is known to be used in ACL reconstruction. The guidewire is threaded through the central (one-way suture passage) of the anchor, and in this variation the guidewire may disable the one-way cams/tabs within the channel that prevent the suture from being pulled proximally when a suture is passed through the channel. For example, the one-way tabs may fold to allow passage over the pin/guidewire. As shown in FIGS. 3A-3P, the guidewire or pin may be used to place or position the anchor into a hole formed in the femoral notch, to place and thereby anchor the ACL graft.

Figure 2B:
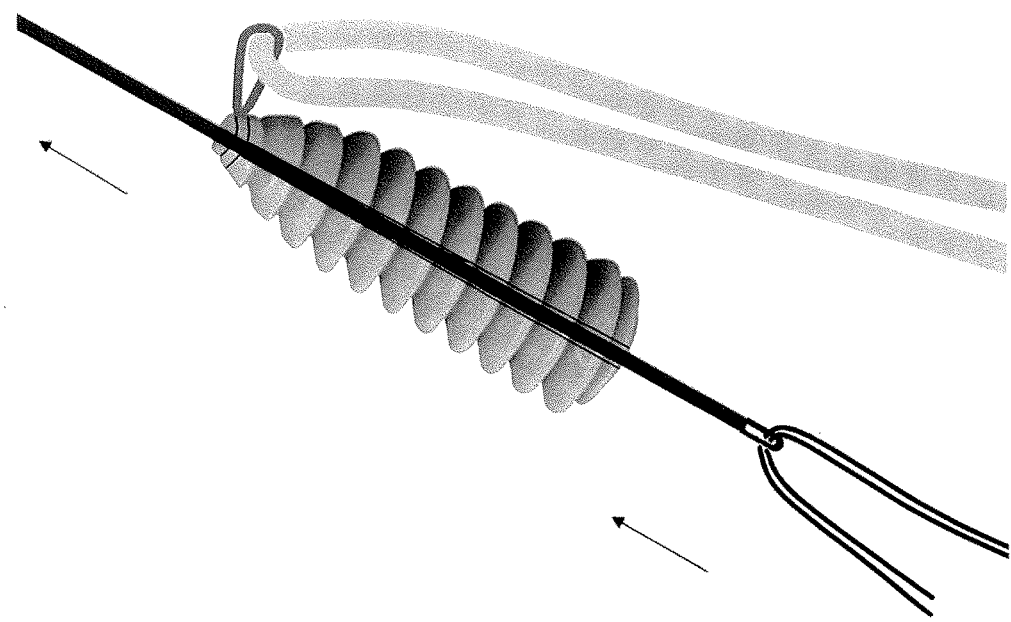
Figure 2C:
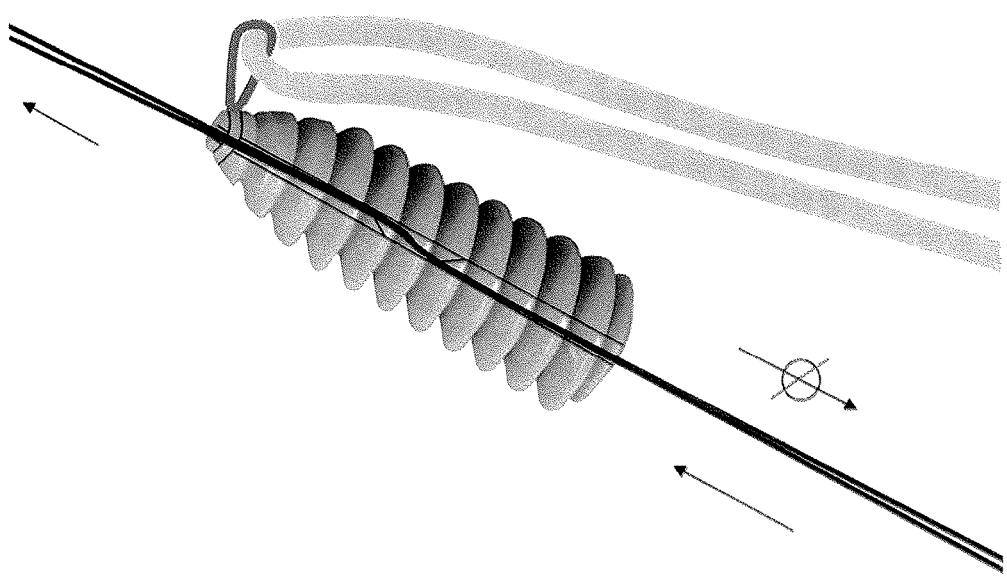
Figure 2D:
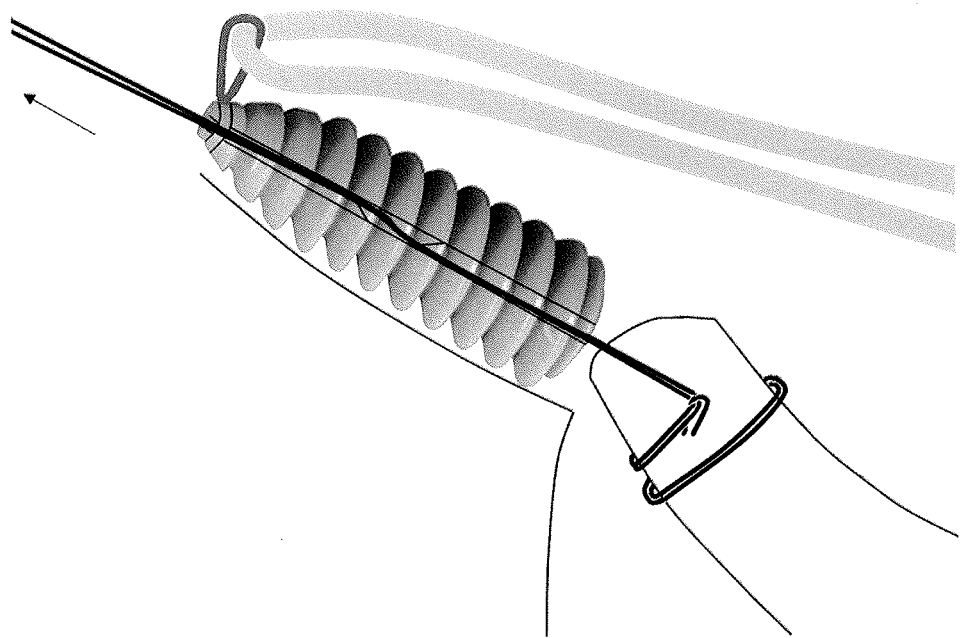

In FIG. 2B, sutures are loaded into the beath pin eyelet and the beath pin (guidewire) is pulled distally through the screw to load the sutures into the anchor, as shown. In this example, the anchor may already be positioned within the notch (not shown), and the sutures may already be secured to the end of the ACL. For example, in FIG. 2C, the sutures are loaded into the anchor, and pulling on the sutures to the left (through the anchor) pulls the ACL tissue toward the anchor base (the proximal end of the anchor) through the suture channel in the anchor, in a one-way, self-tightening fashion. In this example, the suture channel includes cams or tabs that allow the suture to be pulled distally but not proximally, as indicated by the arrow. Eventually, as shown in FIG. 2D, the ACL to which the suture is attached will be pulled adjacent to the proximal end of the anchor (not drawn to scale, as the ACL will typically be much larger than the anchor). In some variations, the ACL may be pulled at least partially into the channel formed in the bone into which the anchor is placed. Once the ACL is pulled (via the suture) adjacent to the anchored scaffolding or graft, it may be sutured to the scaffolding (e.g., graft) using the continuous suture passer, while positioned in the femoral notch.

In one variation, the ACL is sutured to the anchor prior to implanting the anchor in the femoral notch, and the anchor with the end of the femoral notch is then positioned (e.g., by pulling the anchor using a guidewire and or the suture) into position, where it can be expanded or otherwise fixed into position.

FIGS. 3A-3P illustrate one method for repair of an ACL. In this example, the ACL has ruptured proximally within the femoral notch, and the procedure is performed within 3 weeks of the injury. FIG. 3A illustrates a portion of the patient's knee, showing the joint between the femur and the tibia, and in particular illustrating the femoral notch ("notch"). In FIG. 3B the notch is prepared by driving a Beath pin into the posterolateral femoral notch, as shown. Alternatively, the region may be drilled or otherwise penetrated to form a narrow passage through femur head from the femoral notch. In this example, the Beath pin is driven from within the notch and through the femur head region. Another alternative variation is shown in FIG. 2B1, in which the Beath pin (guidewire) is driven from the outer wall of the femur towards the femoral notch (inner wall). In this variation, the approach is from outside of the femoral notch.

Next, as shown in FIG. 2B, the pin is then over-drilled to form a tunnel and/or cavity into which the anchor may be seated; the opening faces the notch. In this example, the cavity is drilled with a bit that is approximately one size smaller than the anchor (a screw-type anchor is illustrated here). For example if the outer diameter of the anchor is about 5-6 mm in diameter, the drill bit diameter may be about 4-5 mm. The depth of drilling may be longer than the length of the anchor. For example, in FIG. 3C-3D, the depth of drilling is approximately 25 mm, as shown in FIG. 3D. In variations in which a transosteal tunnel is formed completely through the femur, a drill may pass completely through the femur. The tunnel may be drilled from the notch side (second side of the bone), as shown in FIG. 3C, or the outer side (first side of the bone), as shown in FIG. 3C1.

In some variations, particularly those in which the scaffold (e.g., graft) attached to the distal tip of the anchor is positioned to the side of the anchor (as illustrated in FIG. 1A), a second cavity may be formed adjacent to the anchor cavity to allow room for the graft. This is shown in FIG. 3E. In this example, a dual barrel impacter is driven (e.g., malleted) along the guide wire (heath pin) to create a second, smaller tunnel just superior to the previously drilled hole. This is shown in FIGS. 3F and 3F1. The graft may fit into the adjacent tunnel without substantially weakening the attachment of the anchor.

Figure 3G:
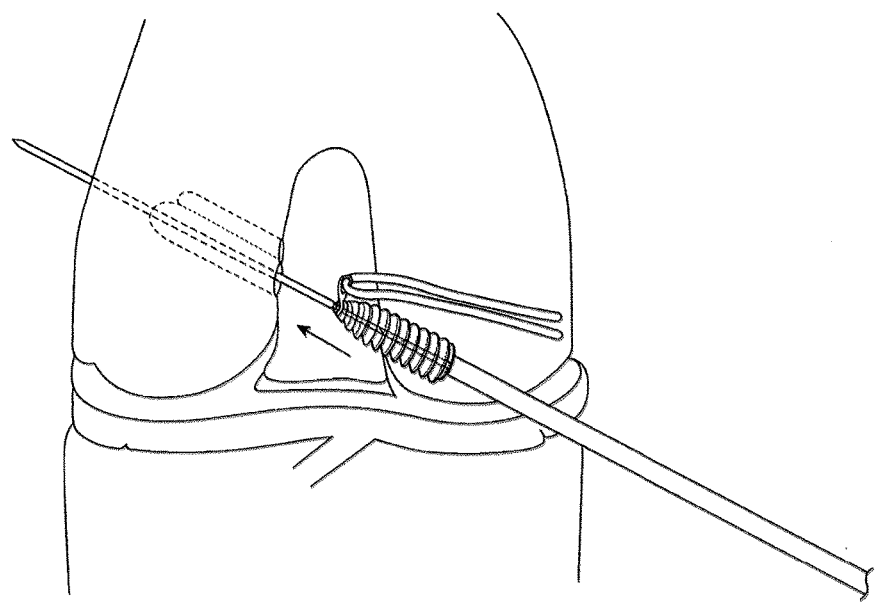
Figure 3H:
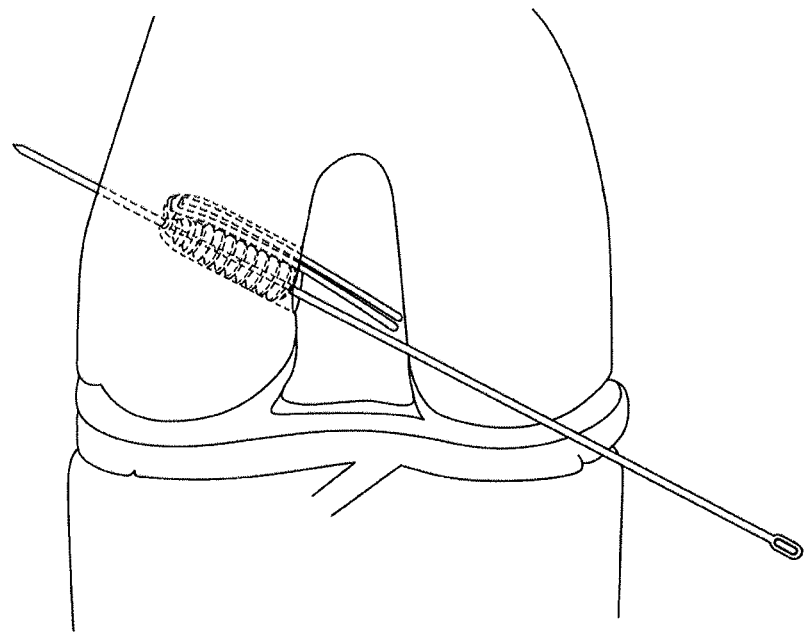

FIG. 3G illustrates the insertion of the knotless screw over the guide wire/pin into the pre drilled hole within the lateral femoral notch; the graft is inserted into the adjacent channel. The anchor and graft may be pushed or pulled (using the guidewire) into position. For example, a pusher may be used to drive the anchor into the channel drilled in the bone. In some variations the anchor is screwed into the channel, over the guidewire; for example an applicator may removably couple with the proximal end of the anchor and allow it to be inserted into the femur by pushing and/or screwing, particularly in the threaded screw-type anchors. The graft, which is coupled to the distal end of the anchor, may stay in the adjacent channel as the anchor is inserted; the coupling region for the scaffold/graft is rotatable relative to the rest of the anchor, thus as the anchor is rotated to insert, the graft may stay in the channel. As shown in FIG. 3H, the reinforcement graft sits snuggly within the pre-punched tunnel just superior to the anchor, allowing optimal in-growth of the graft into the femoral bone.

Once the anchor is secured in the femoral arch, and in variations using a scaffold/graft, with the graft extending from the arch, the end region of the ACL may be pulled into position using a suture. Prior to this step the ACL may be secured with a suture as shown in FIGS. 4A-4D. In FIG. 4A, the ACL is sutured to securely attach the end of the ACL to a doubled-back suture. In this example a continuous suture passer may be used to pass the midpoint of a free suture around and then through the ACL stump, as shown in FIG. 4A. In FIG. 4B, the suture is then fed through the loop to secure the tissue in a self-cinching manner, as shown in FIG. 4C. In some variations, this can be done outside of the knee, without tissue interference, because the suture has been inserted into the knee, passed through the ACL tissue, and removed all through the same single pathway. Finally as shown in FIG. 4D, the ligament is now secured and the sutures are ready to be loaded into the knotless anchor.

Figure 3I:
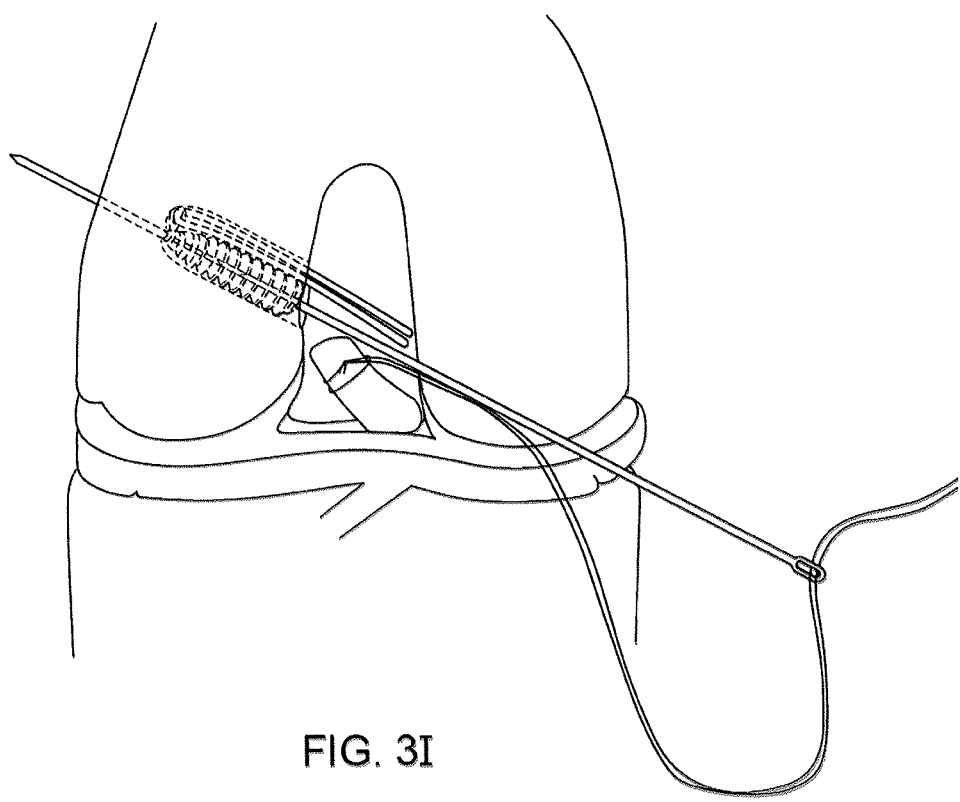
Figure 3J:
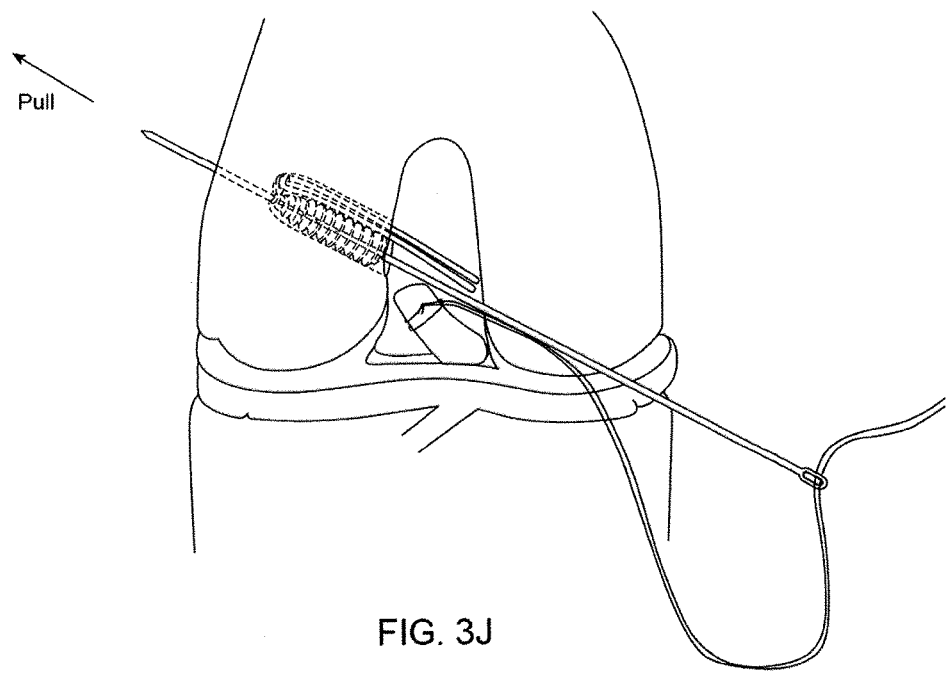
Figure 3K:
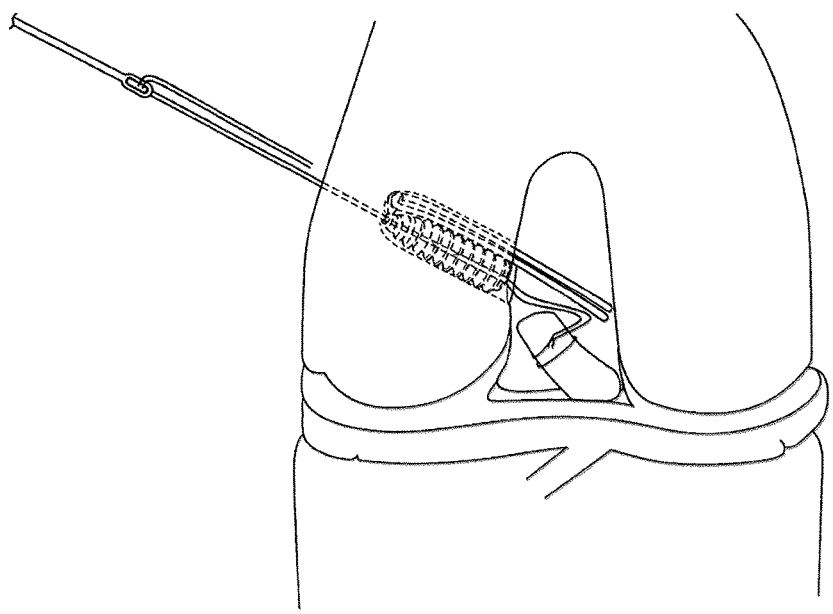
Figure 3L:
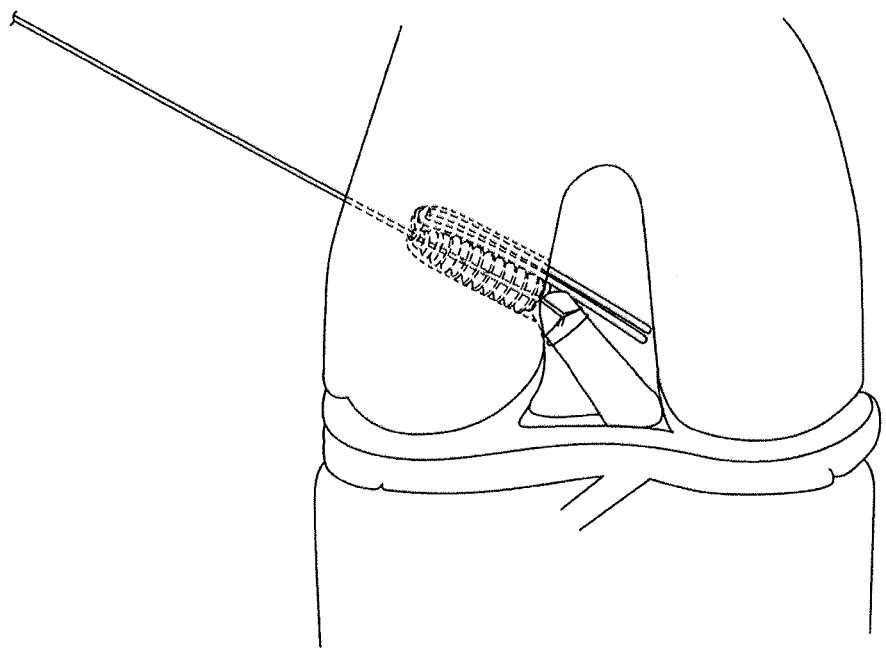

Returning now to FIG. 3I, the suture ends from the previously sewn ACL may then be fed into the eyelet of the beath pin (which may be done outside of the knee), and the beath pin drawn through the anchor (e.g., pulling distally and/or pushing proximally) to draw the ACL to the proximal end of the anchor and adjacent to the graft, as shown in FIG. 3J. For example, the beath pin may then be pulled out from the lateral knee as is typically done with current ACL reconstruction techniques, and the suture follows and is therefore loaded into the anchor. In FIG. 3K, both ends of the suture have been withdrawn through the anchor distally by pulling on beath pin (guidewire) as illustrated. Because the suture channel through the guidewire does not allow the suture(s) to be withdrawn proximally, either or both ends of the suture may be pulled distally to draw the end of the ACL near the proximal end of the anchor within the bone, and adjacent to the graft.

Figure 3M:
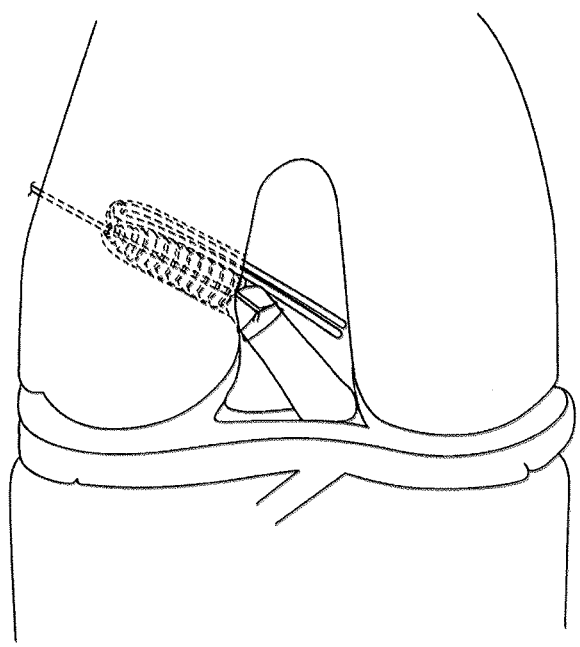

The ligament can be tensioned by pulling on the sutures with the desired amount of force. This may reduce the knee (e.g., pulling the tibia back into position relative to the femur) and may bring the ACL tissue back to its origin on the femoral notch. Thereafter the proximal end of the suture may be knotted and cut, as shown in FIG. 3M. For example, a small (e.g., 2 mm) incision can be made where the sutures exit the skin and any standard arthroscopic knot cutter can be slid down to the lateral femur where the sutures can then be safely cut flush with the bone.

Figure 3N:
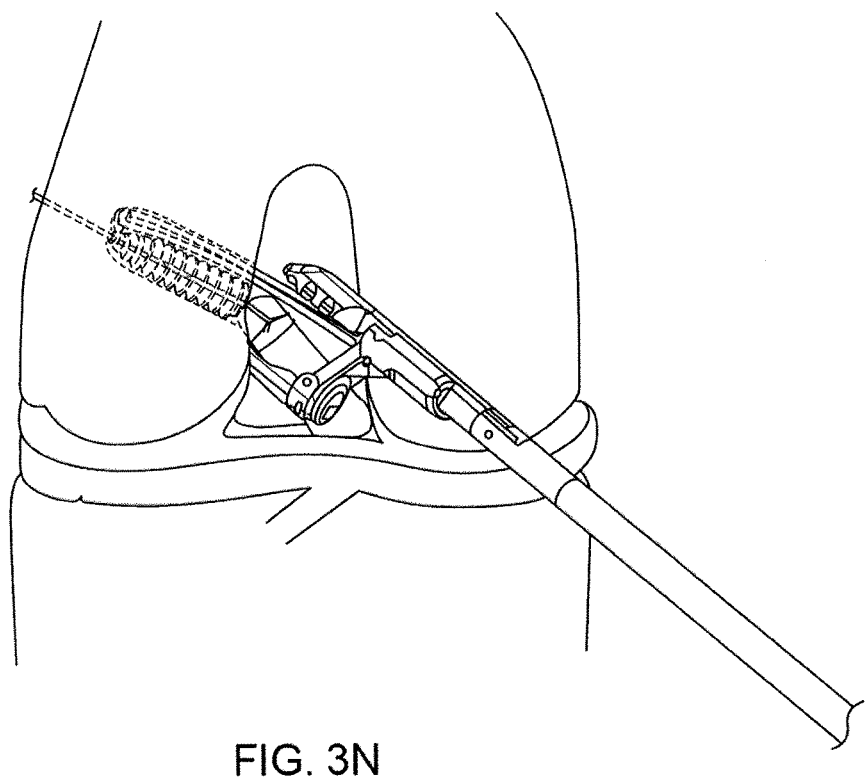
Figure 3O:
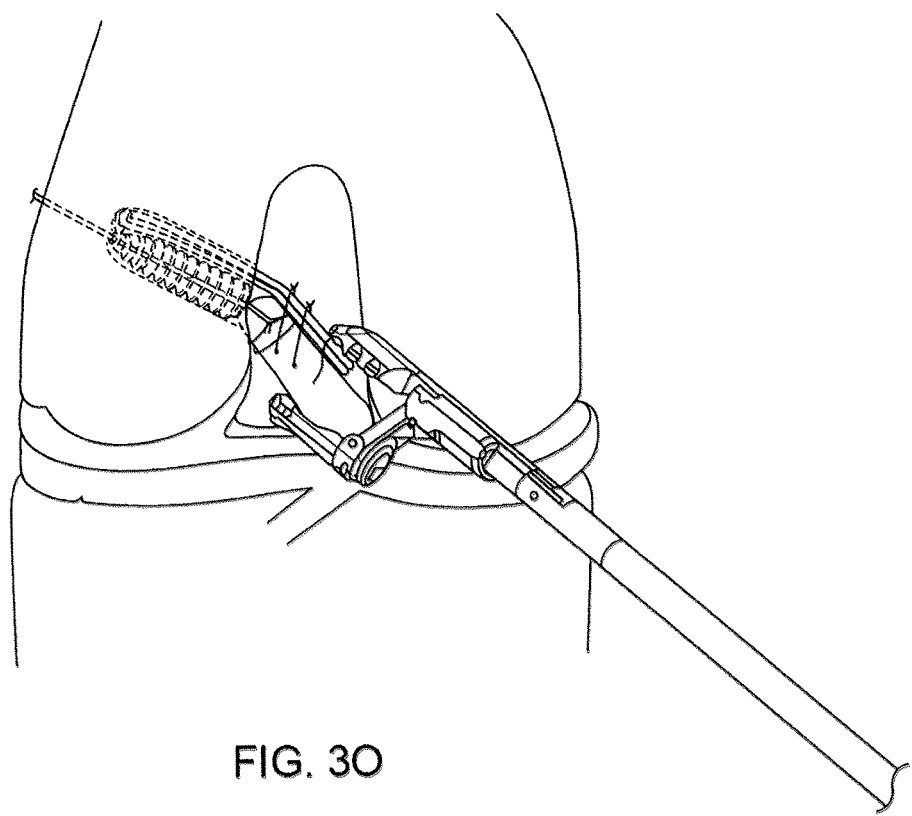
Figure 3P:
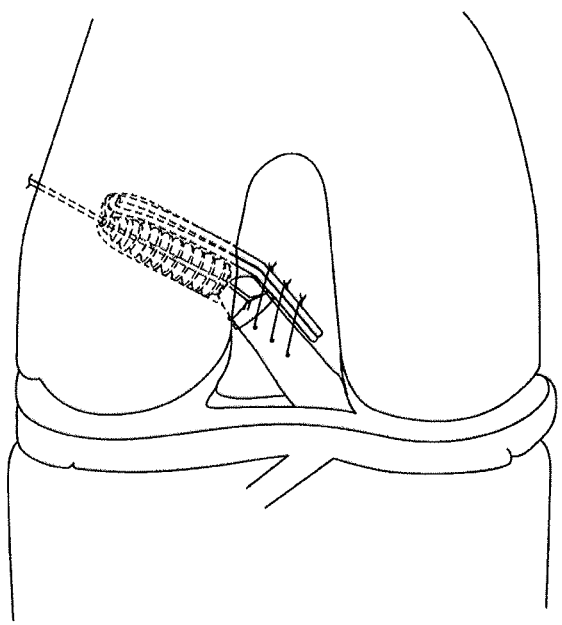

Finally, the ACL can be sutured to the graft/support material, as shown in FIGS. 3N to 3P. In this example, the continuous suture passer is brought in to sew the graft to the ACL to reinforce the repair. The continuous suture passers described herein may be positioned within the notch and still function to pass a suture through the ACL and the graft material, within the limited space of the notch. The final repair allows for a well-tensioned, significantly reinforced ACL repair.

In some variations, platelet-rich plasma or other biologic healing stimulants may also be added following or during the procedure in the notch. Note that FIGS. 3A-3P are not drawn to scale. For illustrative purposes, the screw anchor shown in the figures appears larger than the ligament in the drawings; in actuality the ligament is likely to be considerably larger that the screw.

FIGS. 10A-10K illustrate another variation of a method (and apparatus for performing the method) of repairing a tissue using a transosteal tunnel/anchor. In this example, as above, the tissue being repaired is a torn ACL. As mentioned above, the methods and apparatuses described herein are not limited to ACL repair, but may be used in other bone regions, particularly joints such as the shoulder, wrist, ankle, and hip.

Figure 10A:
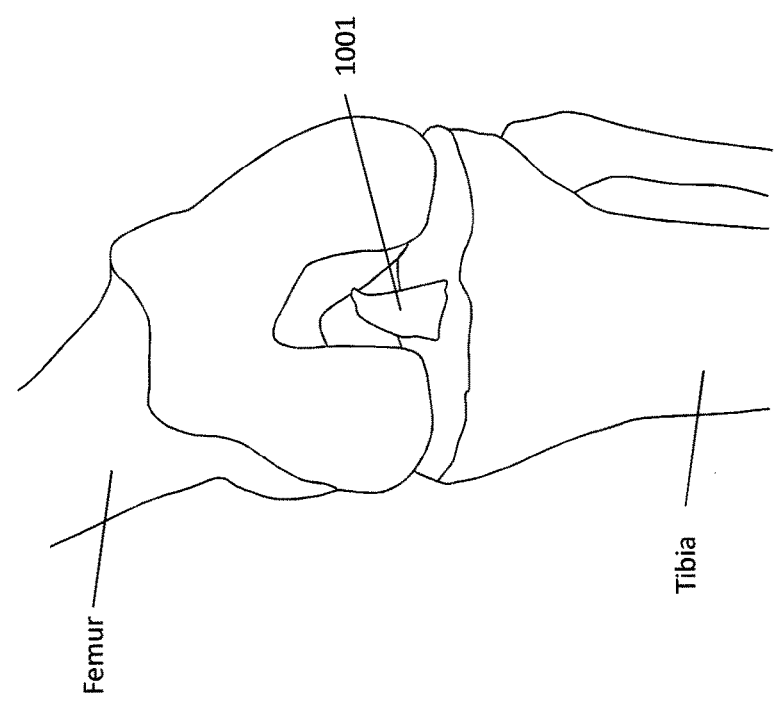
FIGS. 10A-10K illustrate another variation of a transosteal method for repair of a tissue.
Figure 10B:
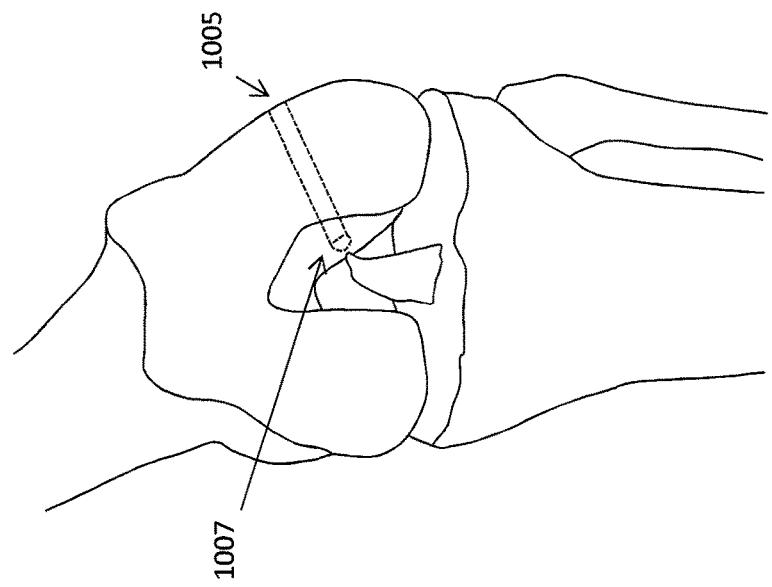

FIG. 10A shows a front view of a subject's left knee. In this example, some of the tissue (e.g., patellar tendon, patella, etc.) are not shown, for clarity; however, the procedure may be performed with them in position. The tibia and femur are illustrated, as the femoral notch. The ACL 1001 is shown, and is torn. As discussed above for FIGS. 3B1 and 3C1, a tunnel may be formed through the bone, either with or without a guidewire/beath pin. FIG. 10B shows the femur with the channel through the bone from the outer side (surface) 1005 extending though the femur head to the inner (notch) side/surface 1007. Thus, the method may include the step of drilling a tunnel (channel) through the bone from first side to second side.

Figure 10D:
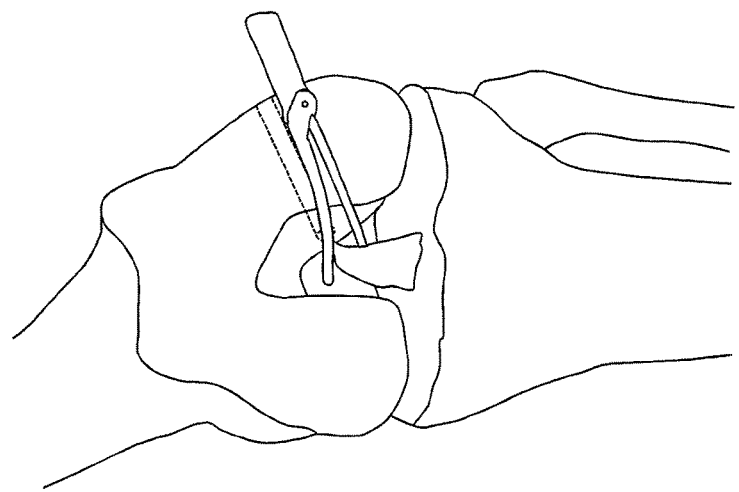
Figure 10C:
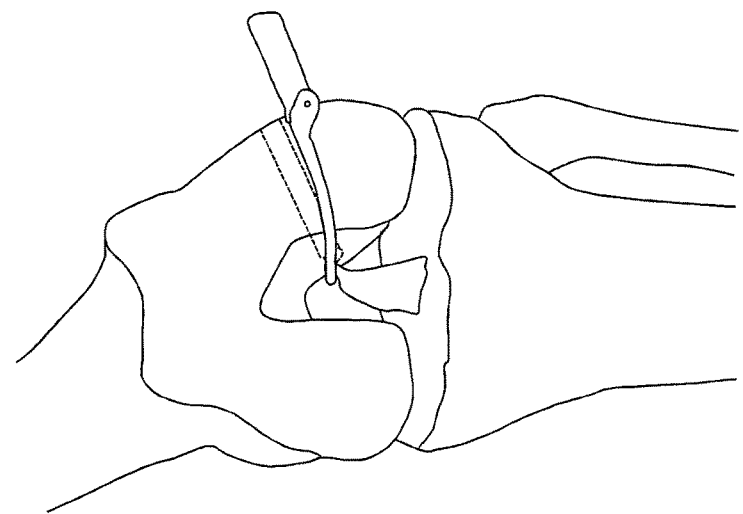
Figure 10E:
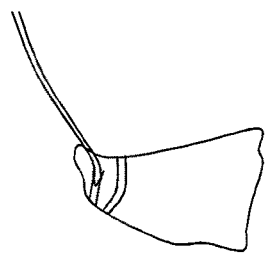
Figure 10E:
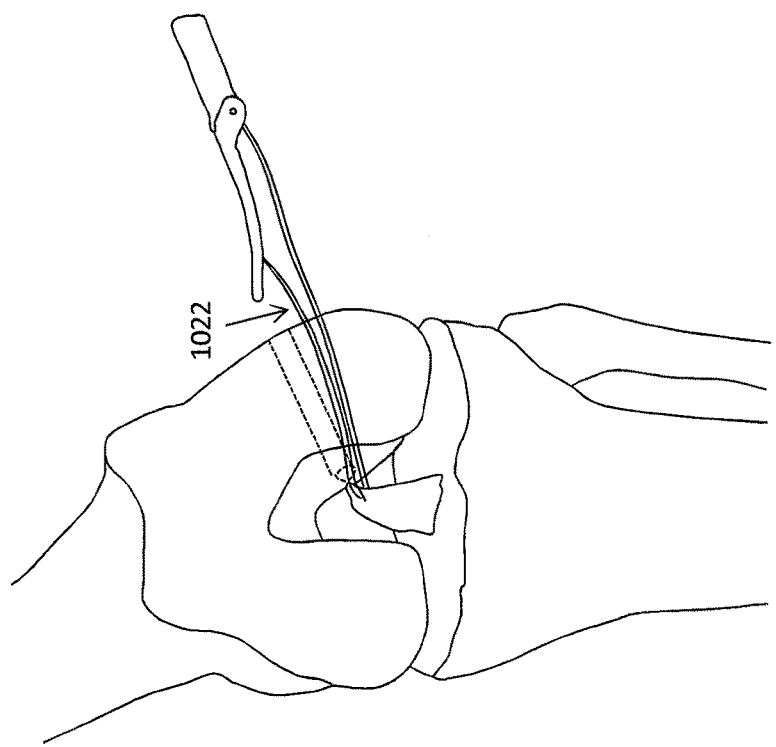

FIG. 10C illustrates the use of a suture passer to secure a suture to the end of the tissue to be attached to the bone. In this example, the suture passer is percutaneously inserted into the femoral notch region. The suture passer used is similar to the suture passer described above in FIGS. 8A-8D. Because the region of the body (e.g., the femoral notch region) is constrained, and may be otherwise difficult to maneuver, a suture passer capable of operating in such a constricted space with a high degree of maneuverability and reliability may be used. For example, in FIG. 10C, the upper jaw member of the suture passer is angled (by pivoting about the proximal elongate body) while the lower jaw is retracted, permitting the upper jaw member to be positioned on one side of the torn tissue (e.g., ACL). Once the upper jaw is positioned, the lower jaw may be extended, as shown in FIG. 10D, to form a distal-facing jaw around the torn tissue. Having the lower jaw retracted may allow the distal end of the suture passer to fit into otherwise difficult (or impossible) to reach regions of the tissue, particularly regions in which the tissue (e.g., bone) forms a bottleneck or constricted region before opening up into a larger space, as is the case in the knee. Once in position around the torn tissue, the suture passer may clamp or hold the end of the torn tissue (by rotating the upper jaw member against the lower jaw member) and the tissue penetrator may be extended across the opening between the jaws and through the tissue to push a loop (bight) of suture through the tissue. The suture may be attached as illustrated in FIGS. 4A-4D, discussed above, and shown in FIGS. 10E and 10E1. In some variations the loop of suture 1022 is pulled by the upper jaw and the ends of the suture may be passed around and through the loop which is then cinched or tightened onto the tissue, as shown in FIG. 10E1. Thus, the suture may be secured by one or more "locking loops" of suture passed by the tissue passer. Additional suture stitches may also be passed to further secure the suture(s) to the torn tissue. The same, or different, sutures (e.g., different lengths of the same suture) may be passed though/around the torn tissue (e.g., ACL).

Figure 10G:
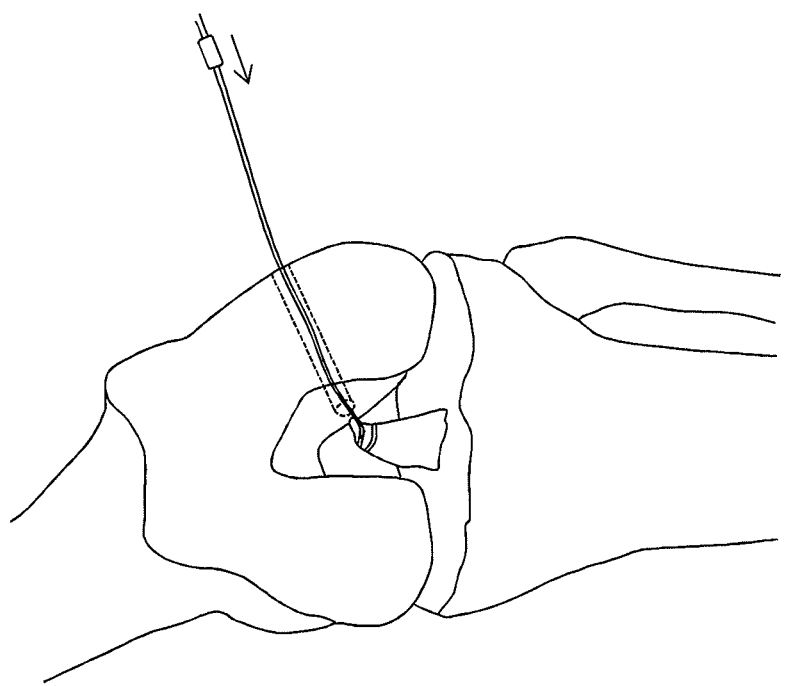
Figure 10F:
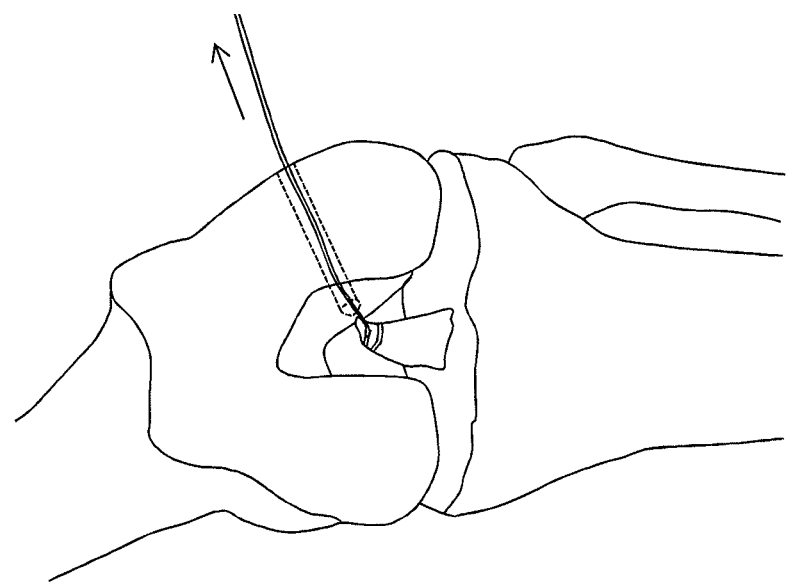

Once the suture has been secured to the torn tissue, the free end(s) of the one or more sutures may be pulled through the bone tunnel from second (e.g., inner) end of bone tunnel to the first (e.g., outer) end of the bone tunnel, as illustrated in FIG. 10F. In some variations the anchor (a transosteal anchor), which may include a scaffold, as discussed above, may have already been passed through the tunnel in the bone and be positioned at the inner end of the bone tunnel (in this example, near the femoral notch). The anchor may be locked or otherwise secured in position so that the suture(s) that attach to the torn tissue may be passed through the anchor and the bone tunnel.

FIG. 10G shows another alternative, in which the anchor is passed into and secured to the end of the bone tunnel after the lengths of suture have been passed through the bone tunnel. In this example, the suture anchor may be pushed or otherwise driven through the bone tunnel along the lengths of suture until it is positioned near the inner face (notch side) facing the torn tissue, as illustrated in FIGS. 10G and 10H. Thus, the step of positioning and/or securing the suture anchor may be performed either before or after suturing the torn tissue. Once positioned, the suture anchor may be locked into place as described above.

Figure 10I:
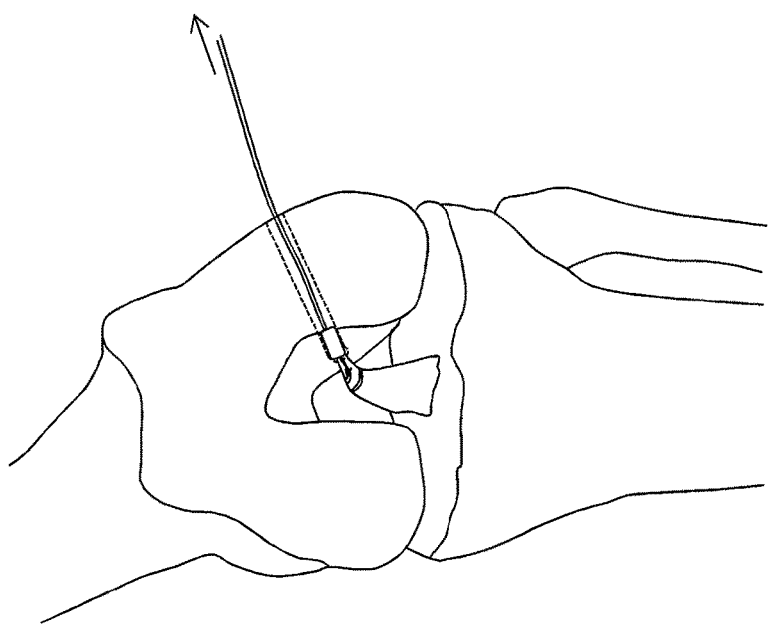
Figure 10H:
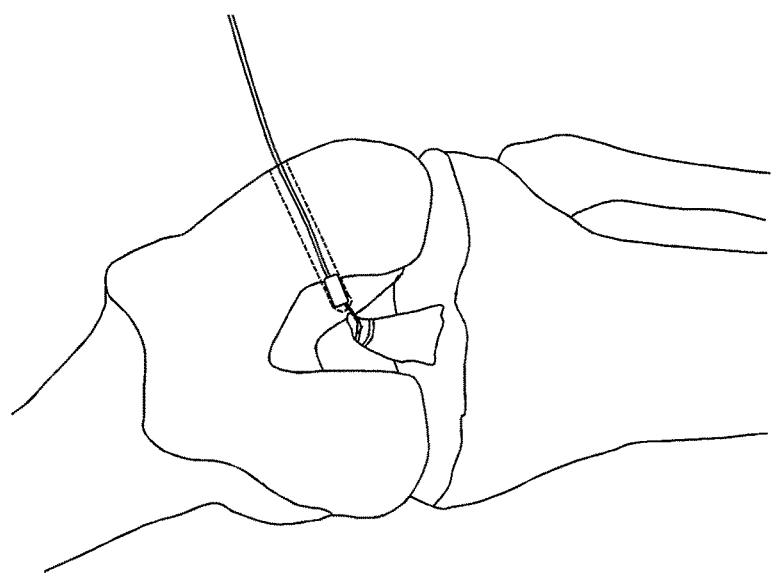

FIG. 10I shows the suture and torn tendon being secured within the anchor/bone by pulling the suture(s) to cinch the suture and/or tissue securely in the suture anchor and thus to and/or in the bone tunnel. In some variations, the tissue may then be further sutured to a scaffold (e.g., graft) that is secured to the suture anchor and/or the bone. Once the torn tissue has been secured as desired, so that the torn tissue is anchored to the bone near the second side of the bone (the side closest to the torn tissue), while allowing the suture to be tightened and adjusted from the opposite side of the bone tunnel (the side furthest from the torn tissue).

Once the torn tissue has been repaired, the loose end of the suture may be cut and/or tied off. FIG. 10J illustrates one variation of the step of trimming all or some of the suture after it has been cinched and lock into the anchor to the appropriate degree. In some variations the suture ends are cut and/or tied off from the outer surface of the bone tunnel; in other variations the suture ends are cut and/or tied off from within the bone tunnel. For example a suture knot may be pushed down the bone tunnel to knot the suture against the suture anchor.

Figure 10K:
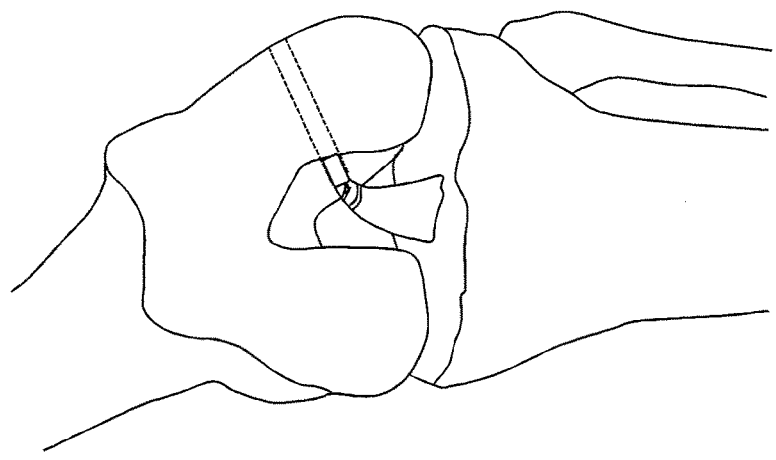
Figure 10J:
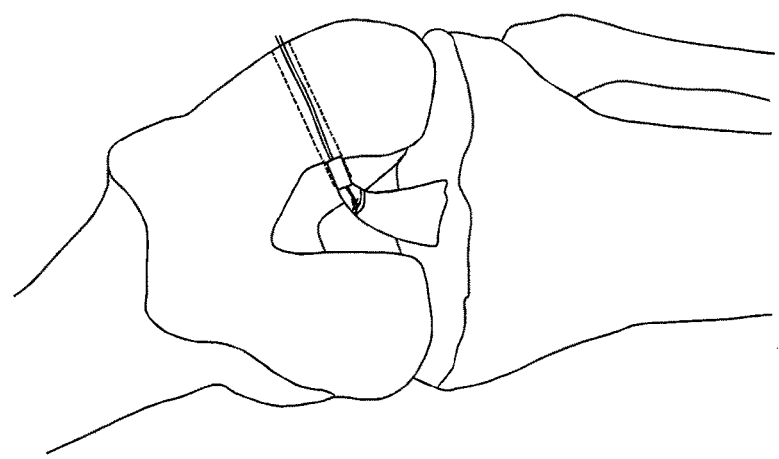

Thereafter, the bone tunnel may be capped and/or filled, as illustrated in FIG. 10K. For example, the bone tunnel may be filled with a bone filler such as a bone cement (e.g., PMMA), and/or bone chips (e.g., xenograft or allograft material), or the like.

Figure 11B:
FIG. 11B shows another variation of an anchor that may be used for transosteal repair.
Figure 11A:
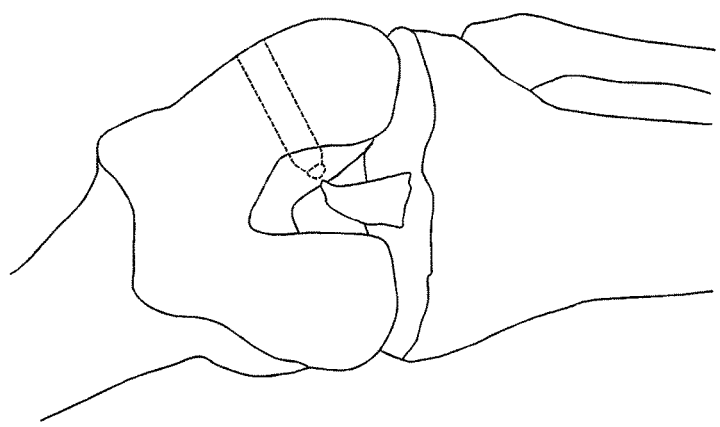
FIG. 11A illustrates an alternative method for repair of a tissue (e.g., ACL) similar to the method shown in FIGS. 10A-10K.

In some variations the tunnel through the bone may have a larger outer surface opening than inner surface opening, as illustrated in FIG. 11A. In this example, the access or opening into the tunnel from the femoral notch side is narrow. This may further assist the anchor in remaining in the tunnel, though adjacent (within a few mm, e.g., within about 5 mm, within about 4 mm, within about 3 mm, within about 2 mm, within about 1 mm, etc.) to the inner bone wall, closest to the tissue to be repaired. In FIG. 11A the tunnel is tapered from a larger diameter to a smaller diameter. In some variations the tunnel includes one or more "steps" in diameter. As mentioned above, in some variations, this region of the bone tunnel may include additional structures for mating with the suture anchor to prevent migration of the suture anchor relative to the bone, such as notches, pits, or the like. These structures may be formed by a drill or by a tamp or other bone-shaping device.

FIG. 11B illustrates another variation of a suture anchor that may be used, in particular, with a tunnel having a tapered end as shown in FIG. 11A. In this example the anchor includes a central passageway through which the suture may pass. The central passageway may include one or more one-way locks or other locking elements to prevent the suture from pulling proximally out of the anchor while allowing the suture to be pulling taught distally, through the bone anchor. One end of the anchor in FIG. 11B is tapered to match the taper in the end of the bone tunnel. In use, the anchor may be inserted (tapered end first) through the bone tunnel from the outer surface, driven along the bone tunnel, until the tapered end of the anchor is within the tapered end of the bone tunnel.

Example 2: Tibial-Sided Transosteal Anchor for Meniscal Root Repair

In some variation, the methods and apparatuses described herein may be used to treat a torn meniscal root. For example, the meniscal root may be repaired as described above by forming a transosteal tunnel through the tibia (e.g., to the tibial plateau) and repairing the meniscal root by suturing the torn end of the root and securing it to an anchor held in tunnel near (e.g., adjacent) to the tibial plateau.

It is well-known in the art that repair of the meniscal root is both desirable and highly difficult. For any patient, even "ideal" young and highly active candidates, meniscal repair continues to represent a significant challenge. It is undisputed that vertical tears greater than 1 cm in the peripheral-third of the meniscus should be repaired, however, there has been new attention on repairing posterior root tears. With these root tear repairs, an inside-out repair is not feasible due to the posterior midline placement of the needles and the passage of the suture. Both the medial and lateral menisci have a stout attachment at their very posterior aspects, which is called the root attachment. The root of the meniscus is the region where the meniscus attaches to the central tibial plateau. This root attachment is important because it holds the meniscus in place, provides stability to the circumferential hoop fibers of the meniscus, and prevents meniscal extrusion. When there is a tear of the meniscal root, it has been demonstrated on biomechanical testing that it is equivalent to having the whole meniscus removed. Thus, a tear of the meniscal root is considered a very serious condition. An example of a meniscal root repair is shown in FIG. 12A.

Meniscal tears within the body of the meniscus or at the meniscocapsular junction represent a well-understood and manageable condition encountered in clinical practice. In comparison, however, meniscal root tears (MRTs) often go unnoticed and represent a unique injury pattern with unique biomechanical consequences. The root attachments of the posterior horns of the medial and lateral meniscus are very important for joint health. When these are torn, the loading of the joint is equivalent to having no meniscus on the affected side. Thus, these patients can often have early onset arthritis, the development of bony edema, insufficiency fractures, and the failure of concurrent cruciate ligament reconstruction grafts. For this reason, much research has gone in to meniscal root repairs over the last several years. However, current methods for repairing the meniscal root are not completely satisfactory. For example, meniscal repair techniques that suture the meniscus from the "outside" (e.g., though the capsule) may not properly restore the anatomy, for example, anchoring the meniscus to the posterior capsule, rather than the tibia.

Figure 12B:
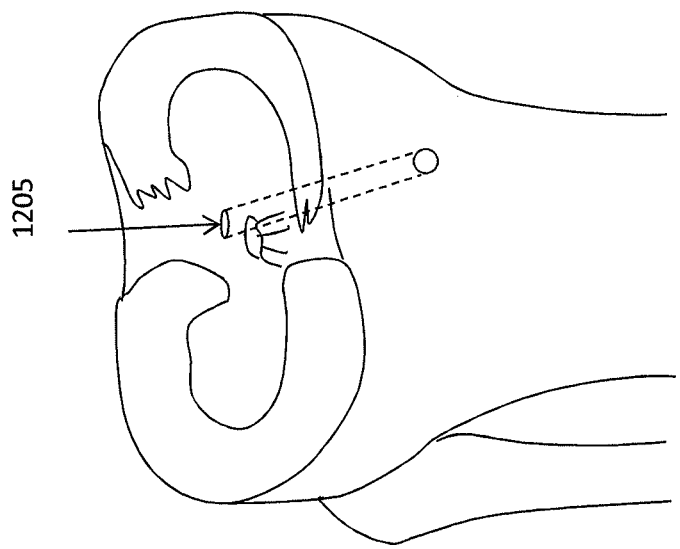
FIG. 12B shows a transosteal tunnel formed through the tibia beneath the torn meniscal root.
Figure 12A:
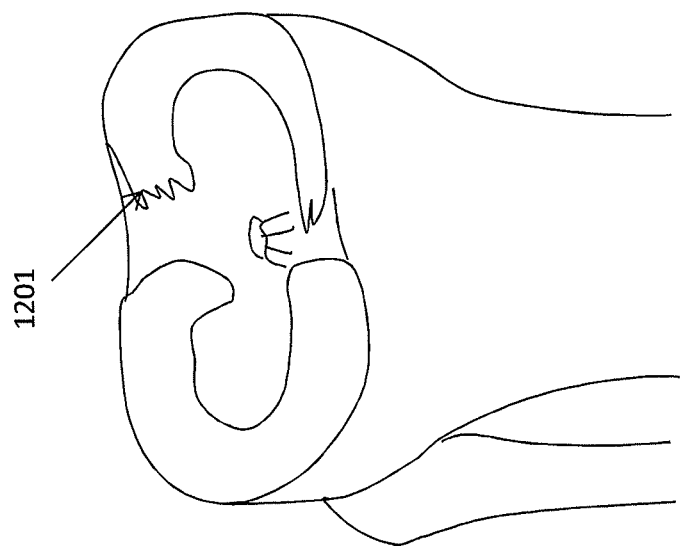
FIG. 12A illustrates an example of a torn meniscal root of a knee.
Figure 12D:
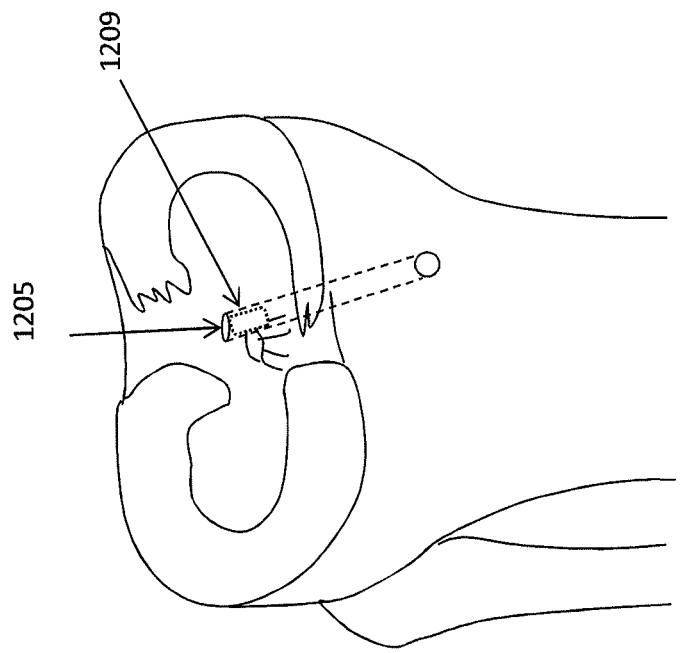
FIGS. 12C and 12D show positioning and securing an anchor near the tibial plateau after inserting from the opposite side of the tibial tunnel.
Figure 12C:
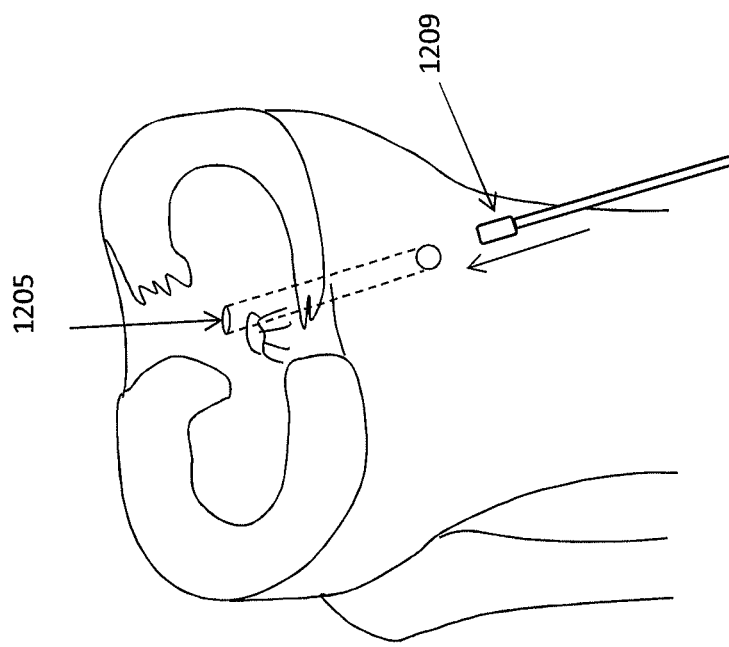

For example, FIG. 12A illustrates a torn meniscal root 1201 in the knee. In this example, the femur is not illustrated; in practice the femur may be positioned over the torn tissue, making it difficult to access, and difficult to place an anchor near the tibial plateau. Instead, prior to the invention described herein, the best that could be achieved was to suture the root and pull the suture (and presumably part of the root) through the trans-tibial tunnel and secure the suture using a button at the side of the tunnel that is furthest from the tibial plateau. As discussed above, this may allow stretch or creep of the sutures securing the tissue, weakening the attachment. FIG. 12B shows the tibia in which a transosteal tunnel has been formed. The tunnel includes an opening 1205 on the tibial plateau that connects to an opening on the side of the tibia. An anchor may be secured adjacent (e.g., flush with, recessed slightly within or extending slightly from) the tibial plateau. FIGS. 12C-12D show an anchor 1209 being secured within the transosteal tunnel through the tibia. The anchor may be placed either before, during or after a suture has been secured to the torn end of the meniscal root. Once the suture has been secured, the meniscal root may be anchored to the tissue anchor and locked into place, so that the meniscal root is anchored to the tibial plateau again. In this example, the anchor, which may be similar to any of the anchors described above, and may include any of these features, such as the central passageway for passing a suture with one-way locks, may be inserted from the side of the transosteal tunnel furthest from the torn tissue and passed through the tunnel and anchored near the distal opening 1205. An applicator 1211 may be used; the applicator may be releasably connected to the anchor and released once the anchor is secured in position. For example, the applicator may connect to the proximal end of the anchor (facing away from the torn tissue). In some variations the applicator may control the release of anchoring members (e.g., extendable arms, etc.) that help to secure the anchor in place.

The transosteal tunnel may be positioned with the opening onto the plateau in any appropriate position, including as close to the original location of the meniscal root attachment site as reasonable. FIGS. 12A-12D are not intended to be representative of the position or the scale.

FIGS. 13A-13E illustrate one method of securing the suture to the torn meniscal root. In this example, the meniscal root is secured to suture using a double locking loop stitch. The root of the meniscus may be arthroscopically repaired using any of the suture passers capable of minimally invasively (e.g., arthroscopically) and being positioned on both the superior and inferior sides of the meniscus and passing a suture between the superior and inferior sides. Examples of these suture passers are described above. In this variation the legs of a loop of suture are each passed between the superior and inferior sides (e.g., from the inferior to the superior side of the meniscus) and then the middle region between the two is passed to form a loop on the superior side. The legs of the suture thus extend from the superior side in two different locations (e.g., radially and/or longitudinally spaced locations) and are pulled though the loop on the superior surface side then the loop is cinched (e.g., by pulling on one or both legs) to tighten it over the legs. The legs may then be secured to the anchor in the tibial tunnel. Alternatively, the legs may be passed after the loop (the region of the suture length between the legs) is passed, or the first (e.g., distal) leg may be passed, then the loop (the region of the suture length proximal to the first leg) then the second (e.g., proximal) leg may be passed. Thus, the order in which the two legs of the suture and the loop region between them are passed between the first and second sides of the tissue may be varied.

Figure 13A:
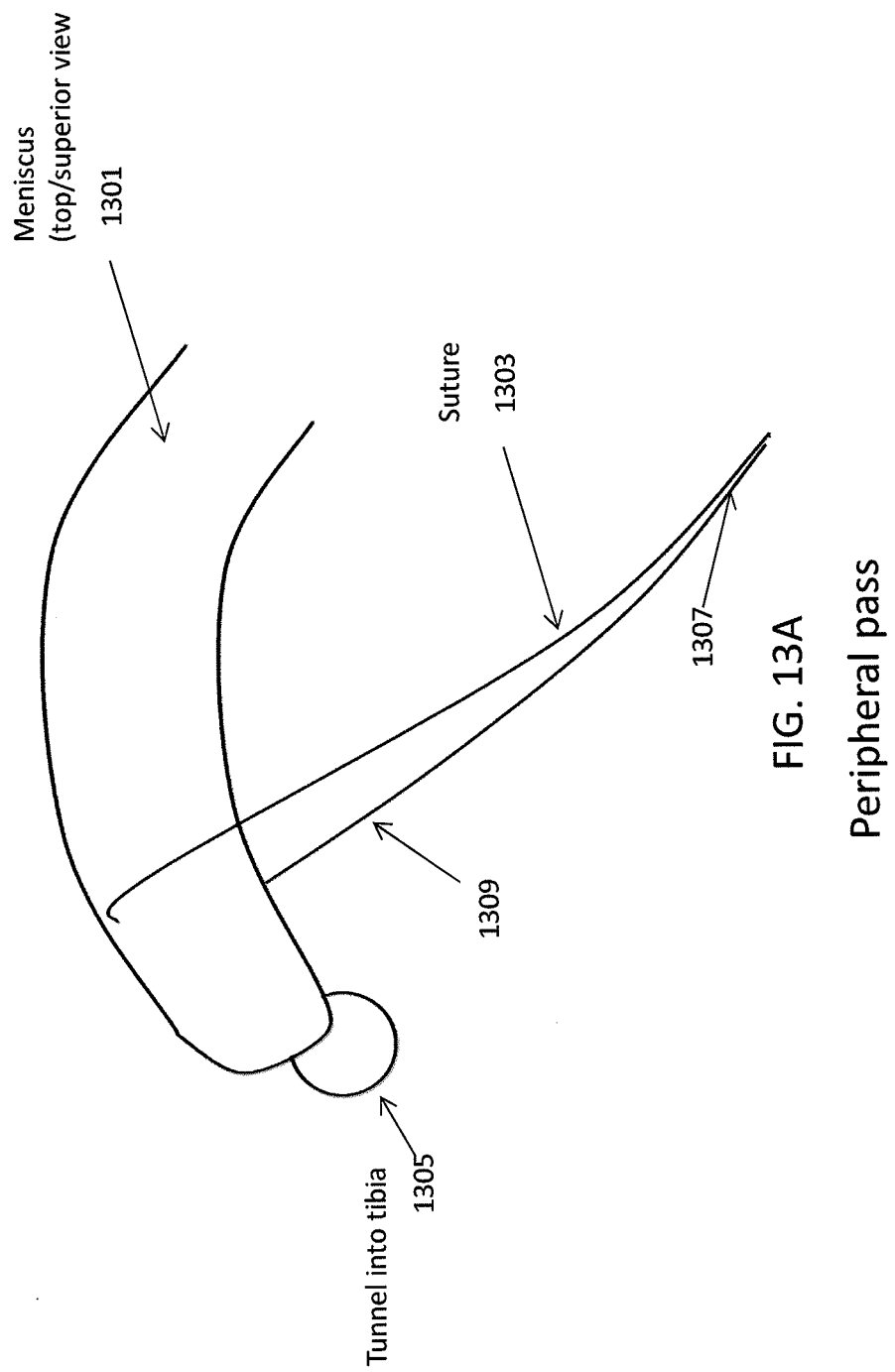

In FIG. 13A, the first leg of the suture 1303 has been passed from the inferior to the superior (top, facing) 1301 surface of the meniscus. As described below, the suture passer may pass a distal "bight" (or loop) of suture by pushing or pulling it through the meniscus once the distal-facing mouth formed by the two jaws of the suture passer have been positioned (e.g., arthroscopically) around the meniscus. For example, the suture passer may arthroscopically access the meniscus of the knee with a first jaw retracted proximally (relative to the proximal-to-distal long axis of the shaft of the device); the second jaw may be bent or bendable (e.g., pivotable) at the distal end region of the shaft of the device. The second jaw may be positioned adjacent to the superior surface either before or concurrently with sliding the first jaw distally to extend it relative to the elongate shaft so that it is extended adjacent to the inferior surface of the meniscus, positioning the meniscus between the distal-facing jaws. The tissue penetrator (e.g., needle) may then push or pull the distal end region of the suture length through meniscus, e.g., from the inferior to the superior surface. If the suture is passed as a loop (e.g., bight) of suture, the distal most end of the suture may be drawn through the tissue until just a single-stranded length of the suture (corresponding to the first leg) passes through the tissue.

Figure 13C:
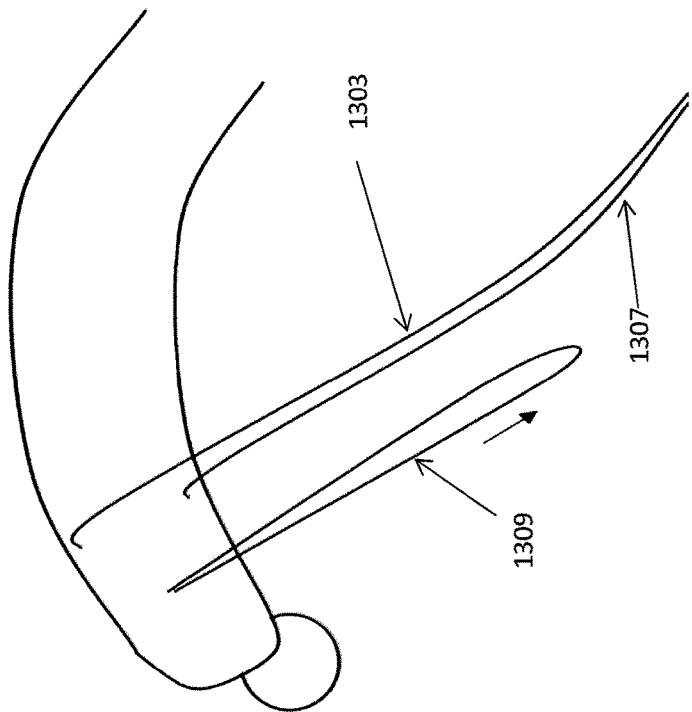
Figure 13B:
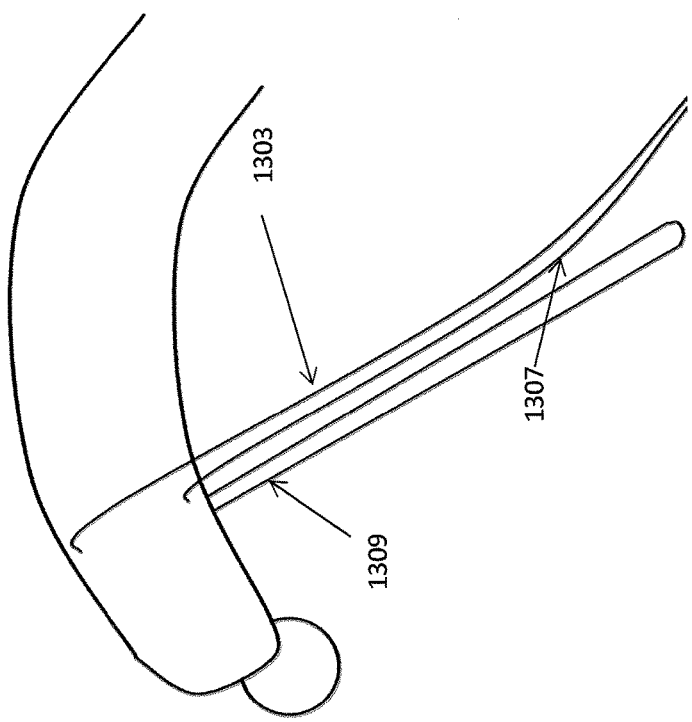

The second leg (e.g., the proximal end region) of the suture has been passed through a radially offset region of the meniscus from the inferior to the superior side as shown in FIG. 13B. In this example, the proximal end region or length 1307 of suture may be loaded on to the suture passer (or it may have been pre-loaded onto the suture passer) and it is extended (e.g., as a bight or loop) though the meniscus from the inferior to the superior surface. The proximal end extended completely out of the meniscus so that both the first leg (the distal length of the suture) and the second leg (the proximal length of the suture) extend out of the superior side. The region between the first and second legs, the middle region, is located on the inferior side and may extend out of the patient, e.g., the access port for arthroscopically accessing the tissue. This central region may then be passed (as a loop or bight) by the same suture passer from the inferior to the superior surface of the meniscus, so that a loop 1309 of the central region of the length of suture also extends from the superior surface of the meniscus, as shown in FIG. 13C. The loop may be passed in a radially intermediate region (between the first and second legs) transversely though the meniscus, as shown. The passage through the meniscus of the loop (and any of the legs) may also be laterally offset relative to the legs.

Thereafter, the first and second legs of the suture may be passed through the loop on the superior surface, as shown in FIG. 13D. This may be performed after withdrawing the suture passer, e.g., by a suture grasping instrument, hook, etc. The loop may then be cinched down over the legs of the suture, as illustrated in FIG. 13E, and the legs secured to the tibia. This may be done concurrently or separately. By pulling the legs of the suture, the loop may be cinched down, and the resulting double locking loop stitch may hold the end of the meniscus so that it can both be repositioned and secured relative to the tibial plateau. Additional sutures (including additional locking loop stitches) may be used.

Once secured, the suture(s) may be pulled through the anchor positioned in the tibial tunnel near the opening 1205 and anchored in place. The free ends of suture may knotted and/or cut. The tunnel may be filled and/or sealed.

In some variations a combination of a locking loop and a second stitch or loop type may be used (e.g. non-locking loop stitch) to secure or repair tissue. The second stitch may be any appropriate type of stitch. For example, FIGS. 13F-13G and FIGS. 13H-13I illustrate two alternative methods in which a locking loop stitch is used with another stitch to secure a meniscal root. For example, in FIG. 13F, the locking loop stitch may be formed as described and illustrated above in FIGS. 13A-13D; either before, after, or during formation of the locking loop stitch 1250, a second stitch, e.g., a simple stitch 1256 may be made through the torn meniscal root. In this example, the simple stitch passes from the inferior side of the meniscus through the tissue, to the superior side of the meniscus, across the superior side, and back down through the meniscal tissue to the inferior side, as shown. This simple (loop or double-pass) stitch may be made with any of the suture devices described herein. Once the stitch is formed, the loose ends of the stitches (both the simple stitch and the locking loop stitch) may be pulled and secured, as illustrated in FIG. 13G. In some variations, it may be beneficial to provide a combination of a locking loop and simple stitch in order to more securely attach the tissue.

FIG. 13H shows another example of a locking loop stitch 1250 and another stitch 1259. As mentioned, the additional stitch may be made before, after, or during formation of the locking loop stitch 1250. In FIG. 13H, the additional stitch is a simple (single loop or one-pass) stitch that traverses from the inferior side of the meniscus to the superior side of the meniscus, and may be formed with any of the suture passer devices described herein or known. All of the free ends of the stitches may be secured, as indicated in FIG. 13I, e.g., by pulling through an opening, e.g., in a tibial tunnel near the opening 1205 and anchored in place.

Figure 14A:
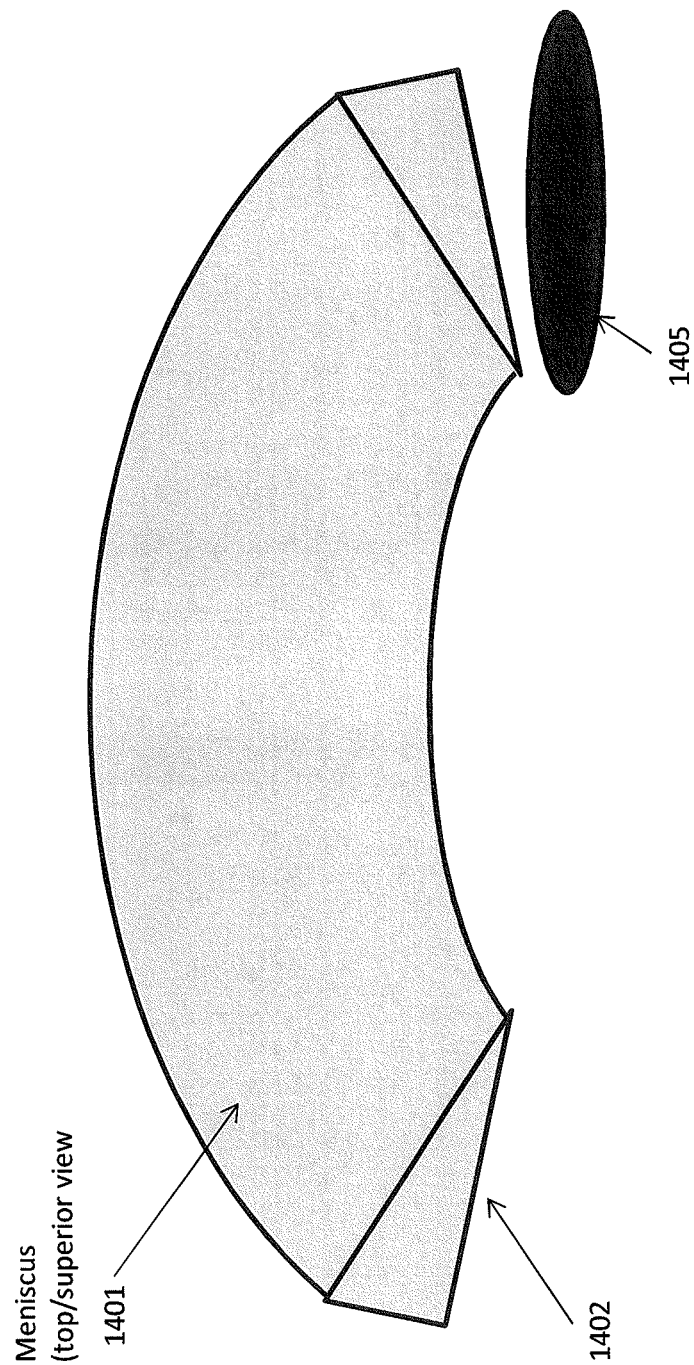
FIGS. 14A-14E show another variation of a meniscal root repair.
Figure 14B:
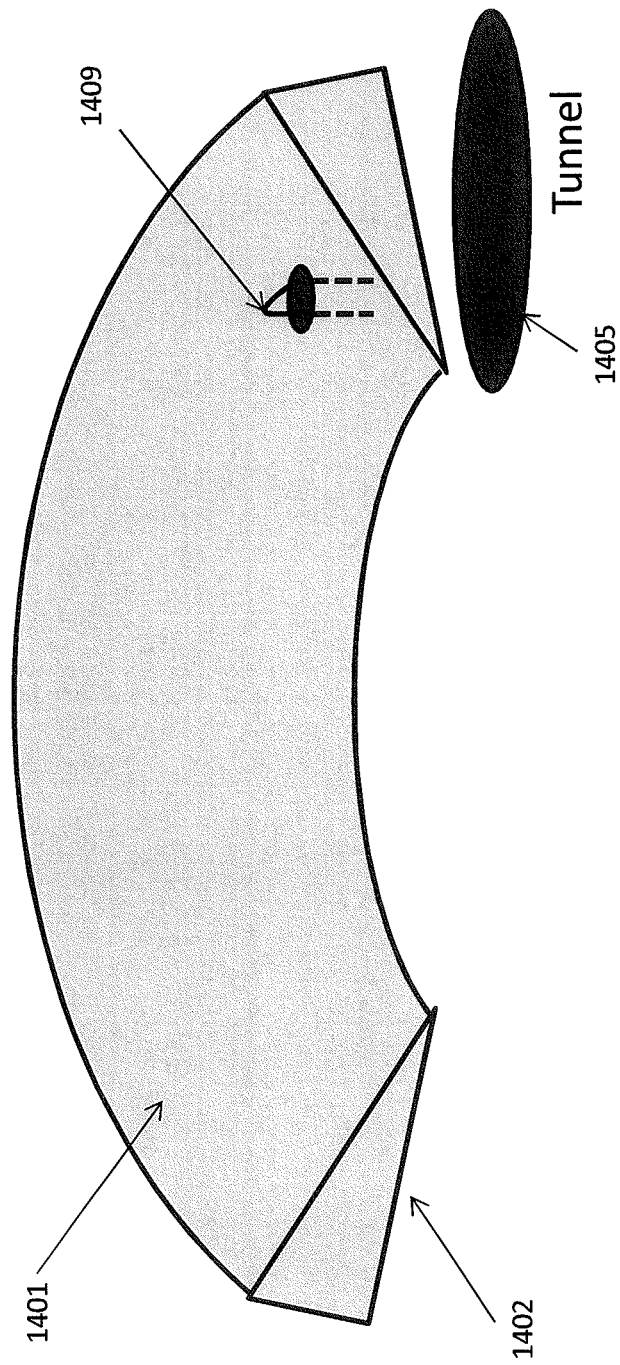

FIGS. 14A-14E illustrate another variation of a meniscal root repair. In this variation, the perspective view shows the top/superior surface of the meniscus as well as the bottom/inferior surface of the meniscus. A tunnel through the tibia 1405 may be formed and an anchor positioned as described above. An access region through the tibia has been formed (tunnel 1405) that may be used to secure the meniscus to the tibial plateau after forming the appropriate locking loop. A suture passer that is configured so that it can arthroscopically be positioned with a first jaw adjacent the superior surface and a second jaw adjacent the inferior surface and pass a length of suture between the superior and inferior surface may be used, and positioned as described above. In this example, the middle region of the length of suture to form the locking loop (double locking look) is passed first, as shown in FIG. 14B. For simplicity in all of these figures, the suture passer is not illustrated, but it operated as described below. Thus, a loop of the middle region 1409 extends from the superior surface as shown. The suture length includes a distal region that will form a first leg and a proximal region that will form a second leg and a central region between the two forming the loop. As the central region loop is passed, the distal and proximal lengths remain outside of the subject, e.g., extending from the arthroscopic access port in the knee used by the suture passer. After passing the loop through the meniscus by the suture passer, the suture passer may be configured so that it releases the loop on the inferior side, allowing it to be repositioned to pass the first and second legs, while leaving the loop on the superior surface.

Figure 14C:
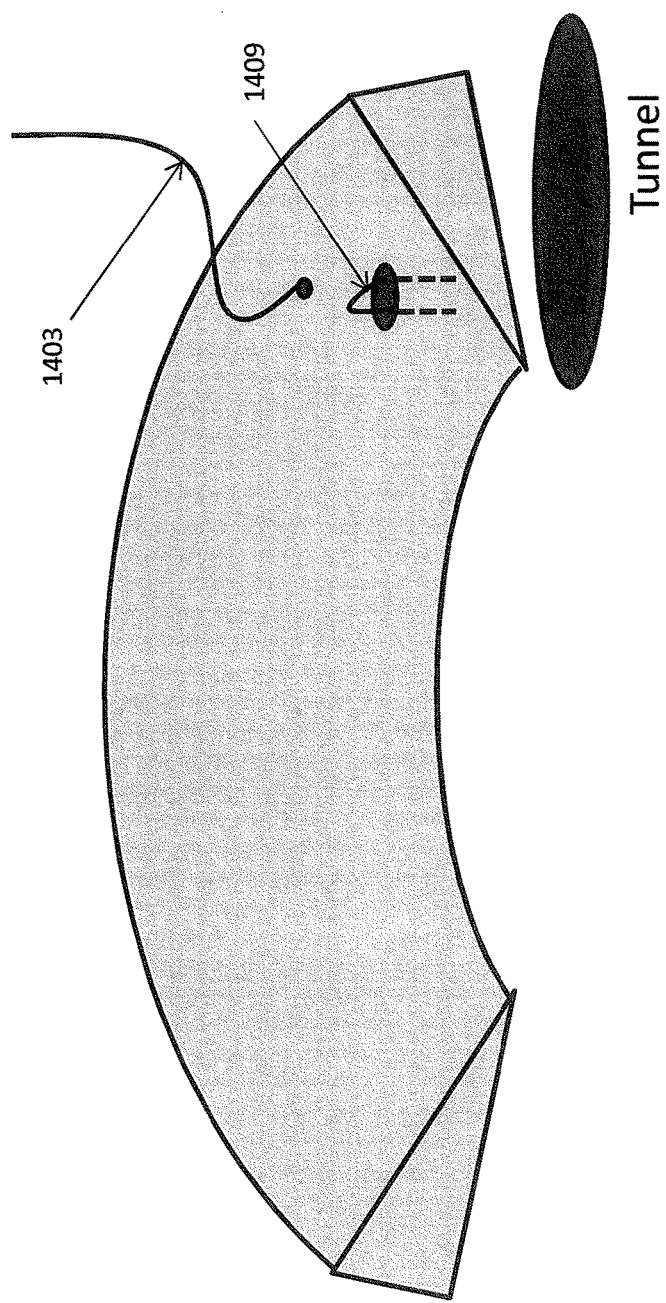

In FIG. 14C the first (e.g., distal) leg of the length of suture has been passed through the meniscus from the inferior to superior side, so that it extends from the superior side. Although only a short length of loop is shown ending form the superior side of the meniscus, the length may be longer. In addition, the figure does not show the adjacent bone regions (e.g., femur head and tibial plateau) that constrain the access to the meniscus, however, however they are typically present. Thus, the free ends of the first and second leg are shown extending away from the meniscus for convenience, in practice, they may be positioned between the superior surface of the meniscus and the femur head.

Figure 14D:
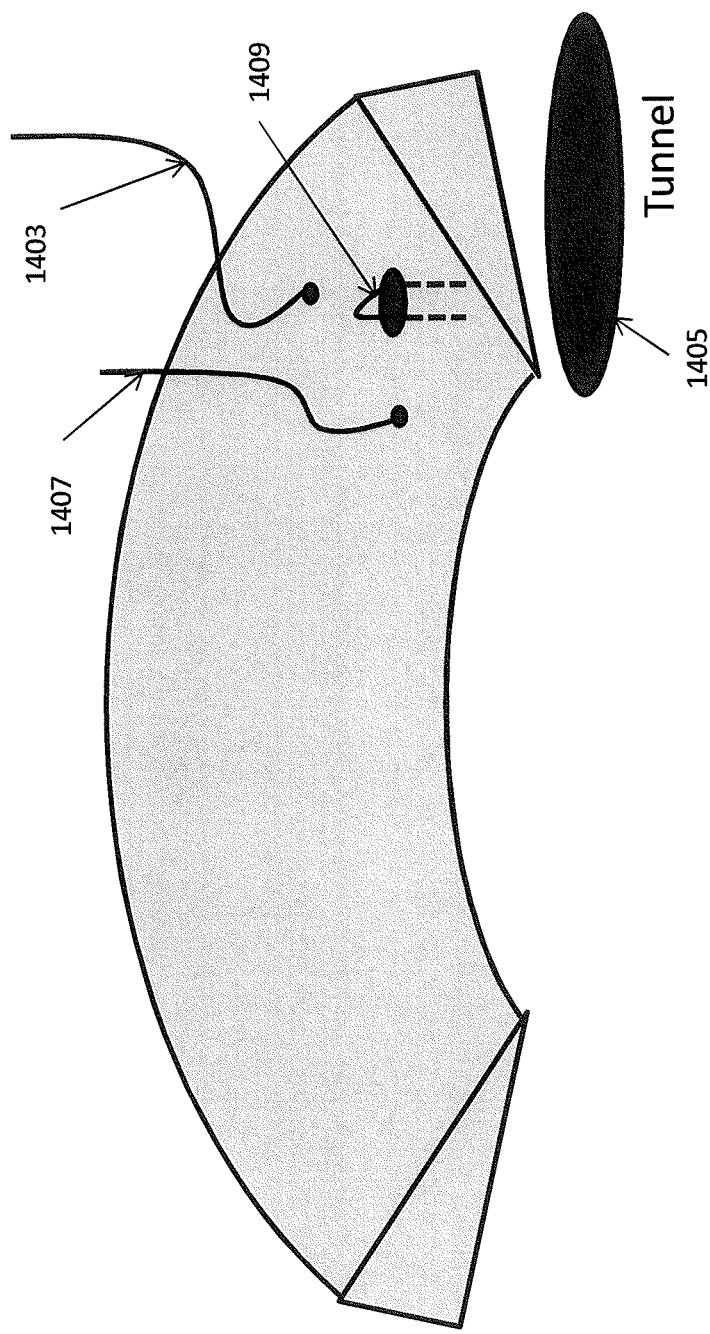
Figure 14E:
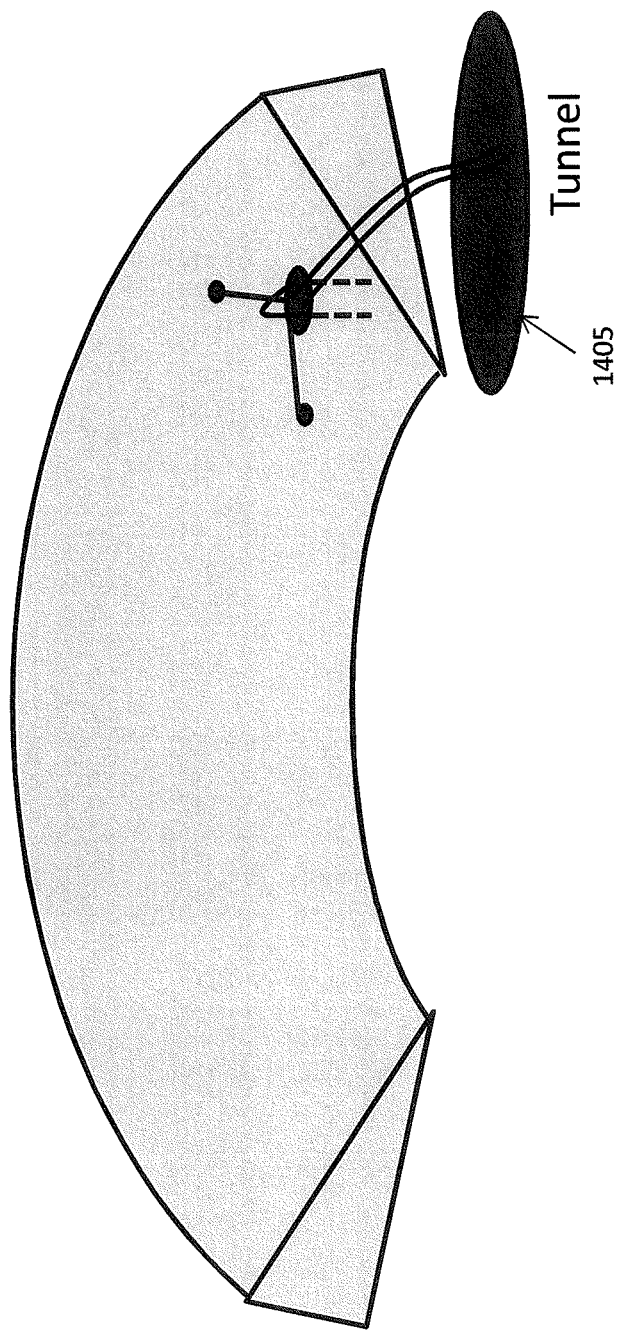

FIG. 14D shows the second leg after it has been passed by the suture passer from the inferior to the superior side of the meniscus. Finally in FIG. 14E, the ends of the first and second leg have been pulled through the loop and into the tibial tunnel 1405, so that they can be used to cinch the loop and secured to hold the meniscus in place. Additional sutures (including additional locking loops) may be used.

The ends of the suture may be passed through the tibial tunnel and anchored to a suture anchor secured within the tibial tunnel. In some variations a guidewire/pin may be used to pull the suture ends thought the tunnel and/or anchor. The anchor may be configured to prevent withdrawal of the suture towards the tibial plateau.

In general, meniscal root repair may require suturing the posterior horn of the meniscus and then anchoring that tissue to the tibia. Traditional bone anchors are inserted into a bone tunnel from the opening that faces the tissue to be anchored. This is not possible in root repair as the constraints within the knee do not allow a straight vector into the tibial plateau at the required insertion point(s). Because of this, the suture may instead be threaded through the tibial tunnel where it exits inferiorly along the side of the tibia. It is then placed in tension around a button with an O.D. greater than the tunnel I.D. As a result, there are several inches of "free" suture from the meniscal tissue to the fixation at the button. Under loading, we have observed that this free suture stretches. The absolute distance that this free suture can stretch is a function of the length of the free suture. For example, depending on the modulus of elasticity of the suture material, if the function is linear and there is a 10% increase in length at a given load (hypothetically), 1 mm of suture will only creep 0.1 mm, but 4 inches of suture will stretch 0.4 inches (1 cm). At some point, this stretch may be clinically significant. The methods and apparatuses described herein may allow a substantial reduction in the length of free suture by placing the transosteal anchor closer to the origin of the tunnel, which will provide a more stable and physiological repair.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for transosteally repairing a tissue, the method comprising:
    forming a tunnel through a bone so that the tunnel extends from a first side of the bone to a second side of the bone;
    passing a suture anchor through the tunnel and adjacent to the second side of the bone;
    securing the suture anchor within the tunnel adjacent to the second side of the bone;
    securing a torn end of the tissue to a suture; and
    cinching the suture in the suture anchor by pulling the suture from outside and adjacent the second side of the bone through the anchor and out of the first side of the bone.

2. The method of claim 1, further comprising securing the torn end of the tissue to a graft coupled to the anchor.

3. The method of claim 1, wherein forming a tunnel comprises drilling an elongate, straight tunnel through the bone.

4. The method of claim 1, wherein forming a tunnel comprises drilling an elongate, straight tunnel through the bone from the first side of the bone to the second side of the bone.

5. The method of claim 1, wherein forming a tunnel comprises forming the tunnel so that an opening into the tunnel on the first side of the bone is larger than an opening into the tunnel on the second side of the bone.

6. The method of claim 1, wherein forming a tunnel comprises driving a guidewire through the bone from the first side of the bone to the second side of the bone.

7. The method of claim 1, wherein passing a suture anchor comprises passing a suture anchor having a central passageway configured to permit a suture to be pulled in a first direction while preventing the suture from being pulled in a second direction that is opposite to the first direction.

8. The method of claim 1, wherein passing the suture anchor comprises screwing the suture anchor in the tunnel.

9. The method of claim 1, wherein securing the suture anchor within the tunnel adjacent to the second side of the bone comprises extending one or more locking arms from the suture anchor once it has been positioned adjacent to the second side of the bone.

10. The method of claim 1, wherein securing the suture anchor within the tunnel adjacent to the second side of the bone comprises securing the suture anchor so that the suture anchor is recessed within the tunnel relative to the second side of the bone.

11. The method of claim 1, wherein securing a torn end of the tissue to a suture comprises percutaneously suturing the torn end of the tissue with a suture passer near the second side of the bone.

12. The method of claim 1, further comprising cutting the end of the suture extending from the first side of the bone.

13. A method for the transosteal repairing a torn anterior cruciate ligament (ACL), the method comprising:
    forming a tunnel through a femur so that the tunnel extends from a first side of the femur to a second side of the femur;
    passing a suture anchor through the tunnel and securing the suture anchor within the tunnel near the second side of the femur;
    securing a torn end of the ACL to a suture; and anchoring the suture in the suture anchor by pulling the suture through the anchor from the second side of the femur and out of the first side of the femur, wherein the anchor comprises a one-way lock configured to prevent the suture from pulling out of the anchor toward the second side of the femur.

14. A method for transosteally repairing an anterior cruciate ligament (ACL) within the femoral notch, the method comprising:

forming a tunnel through a femur so that the tunnel extends from a first side of the femur to a second side of the femur within the femoral notch;

anchoring a suture anchor within the tunnel and adjacent to the second side of the femur;

securing the suture anchor within the tunnel adjacent to the second side of the femur;

securing a torn end of the ACL to a suture; and cinching the suture in the suture anchor by pulling the suture through the anchor from the second side of the femur and out of the first side of the femur, wherein the anchor comprises a one-way lock configured to prevent the suture from pulling out of the anchor toward the second side of the femur.

* * * * *

UNITED STATES PATENT AND TRADEMARK OFFICE
CERTIFICATE OF CORRECTION

PATENT NO. : 9,913,638 B2
APPLICATION NO. : 14/451293
DATED : March 13, 2018
INVENTOR(S) : Saliman et al.

Page 1 of 1

It is certified that error appears in the above-identified patent and that said Letters Patent is hereby corrected as shown below:

In the Claims

Claim 1, Column 26, Line 16; after "suture anchor by" and before "the", delete "puffing" and insert --pulling--.

Signed and Sealed this
Twenty-sixth Day of March, 2019

Andrei Iancu
*Director of the United States Patent and Trademark Office*